US012728253B2

(12) United States Patent
Pun et al.

(10) Patent No.: US 12,728,253 B2
(45) Date of Patent: Sep. 8, 2026

(54) DISINFECTING CAP

(71) Applicant: Medline Industries, LP, Northfield, IL (US)

(72) Inventors: Yushek Pun, Dayton, NJ (US); Joseph Guerrero, Edison, NJ (US); Alexander Vincent Redfield, Carneys Point, NJ (US); Bridget Kelley, Chicago, IL (US); William Kyle Hyland, Oceanport, NJ (US)

(73) Assignee: Medline Industries, LP, Northfield, IL (US)

( * ) Notice: Subject to any disclaimer, the term of this patent is extended or adjusted under 35 U.S.C. 154(b) by 925 days.

(21) Appl. No.: 17/981,328

(22) Filed: Nov. 4, 2022

(65) Prior Publication Data

US 2023/0146509 A1 May 11, 2023

Related U.S. Application Data

(60) Provisional application No. 63/276,195, filed on Nov. 5, 2021.

(51) Int. Cl.
*A61M 39/16* (2006.01)
*A61L 2/18* (2026.01)
(Continued)

(52) U.S. Cl.
CPC ............. *A61M 39/162* (2013.01); *A61L 2/18* (2013.01); *A61L 2/26* (2013.01); *A61M 39/20* (2013.01); *A61L 2103/15* (2026.01)

(58) Field of Classification Search
CPC .... A61M 39/162; A61M 39/20; A61M 39/16; A61M 39/165; A61M 2039/0288;
(Continued)

(56) References Cited

U.S. PATENT DOCUMENTS

| | | | |
|---|---|---|---|
| 877,946 | A | 2/1908 | Overton |
| 2,735,427 | A | 2/1956 | Sullivan |

(Continued)

FOREIGN PATENT DOCUMENTS

| | | | |
|---|---|---|---|
| AU | 2001273300 | B2 | 1/2002 |
| AU | 2012258435 | A1 | 12/2012 |

(Continued)

OTHER PUBLICATIONS

International Search Report and Written Opinion of the International Searching Authority; International Patent Application No. PCT/US2022/049051; Medline Industries, LP; Pun, Yushek, et al.; dated Feb. 23, 2023.

(Continued)

*Primary Examiner* — Chelsea E Stinson
*Assistant Examiner* — Eric A Lange
(74) *Attorney, Agent, or Firm* — SandBright Intellectual Property; Robert D. Spendlove

(57) ABSTRACT

A device for cleaning medical implements is disclosed, in particular a device for cleaning vascular or other fluid access sites. The device includes a cap having an opening to receive an access site. The cap may be used in the following manner: A healthcare worker may, with gloved hands, open the cap packaging and place the cap over the port of a medical implement to be cleaned. The healthcare worker may wipe the site by either applying a turning motion or by simply pushing the cap onto the port. A cap in place on a medical implement may be a positive indication that a desired site of the medical implement is clean. The cap may include a disinfecting substance. Embodiments of the cap may comprise a cap body and a skirt.

19 Claims, 21 Drawing Sheets

(51) Int. Cl.
*A61L 2/26* (2006.01)
*A61M 39/20* (2006.01)
*A61L 103/15* (2026.01)

(58) Field of Classification Search
CPC .. A61M 2039/0285; A61M 2205/0205; A61M 209/06; A61M 2209/10; A61M 2202/18; A61M 2005/3103; A61M 2005/3104; A61M 2005/3106; A61M 2005/3118; A61M 2005/312; A61L 2/18; A61L 2/26; A61L 2202/24; A61L 2/186; A61L 2202/00
See application file for complete search history.

(56) References Cited

U.S. PATENT DOCUMENTS 2,851,036 A 9/1958 Lipari
4,243,035 A 1/1981 Barrettt
4,317,446 A 3/1982 Ambrosio et al.
4,335,756 A 6/1982 Sharp et al.
4,340,148 A 7/1982 Beckham
4,440,207 A 4/1984 Genatempo et al.
4,624,664 A 11/1986 Peluso
4,799,926 A 1/1989 Haber
5,187,843 A 2/1993 Lynch
5,471,706 A 12/1995 Wallock et al.
5,694,978 A 12/1997 Heilmann et al.
5,820,604 A 10/1998 Fox et al.
5,827,244 A 10/1998 Boettger
5,941,857 A 8/1999 Nguyen et al.
5,989,229 A 11/1999 Chiappetta
6,045,539 A 4/2000 Menyhay
6,126,640 A 10/2000 Tucker et al.
6,152,913 A 11/2000 Feith et al.
6,419,825 B1 7/2002 Hahmann et al.
6,592,564 B2 7/2003 Finch et al.
6,679,870 B1 1/2004 Finch et al.
6,685,694 B2 2/2004 Finch et al.
7,282,186 B2 10/2007 Lake, Jr. et al.
D607,325 S 1/2010 Rogers et al.
7,763,006 B2 7/2010 Tennican
7,780,794 B2 8/2010 Rogers et al.
7,794,675 B2 9/2010 Lynn
7,799,010 B2 9/2010 Tennican
7,857,793 B2 12/2010 Raulerson et al.
7,922,701 B2 4/2011 Buchman
7,972,322 B2 7/2011 Tennican
7,985,302 B2 7/2011 Rogers et al.
8,065,773 B2 11/2011 Vaillancourt et al.
8,069,523 B2 12/2011 Vaillancourt et al.
8,083,729 B2 12/2011 Colantonio et al.
8,162,899 B2 4/2012 Tennican
8,167,847 B2 5/2012 Anderson et al.
8,172,825 B2 5/2012 Solomon et al.
8,177,761 B2 5/2012 Howlett et al.
8,197,749 B2 6/2012 Howlett et al.
8,206,514 B2 6/2012 Rogers et al.
8,231,587 B2 7/2012 Solomon et al.
8,231,602 B2 7/2012 Anderson et al.
8,252,247 B2 8/2012 Ferlic
8,262,643 B2 9/2012 Tennican
8,273,303 B2 9/2012 Ferlic et al.
8,328,767 B2 12/2012 Solomon et al.
8,336,151 B2 12/2012 Kerr et al.
8,336,152 B2 12/2012 Vaillancourt et al.
8,343,112 B2 1/2013 Solomon et al.
8,361,408 B2 1/2013 Lynn
8,388,894 B2 3/2013 Colantonio et al.
8,419,713 B1 4/2013 Solomon et al.
8,480,968 B2 7/2013 Lynn
8,491,546 B2 7/2013 Hoang et al.
8,523,830 B2 9/2013 Solomon et al.
8,523,831 B2 9/2013 Solomon et al.
8,641,681 B2 2/2014 Solomon et al.
8,647,308 B2 2/2014 Solomon et al.
8,647,326 B2 2/2014 Solomon et al.
8,671,496 B2 3/2014 Vaillancourt et al.
8,728,056 B2 5/2014 Colantonio et al.
8,740,864 B2 6/2014 Hoang et al.
8,777,504 B2 7/2014 Shaw et al.
8,808,637 B2 8/2014 Ferlic
8,828,327 B2 9/2014 Colantonio et al.
8,832,894 B2 9/2014 Rogers et al.
8,834,650 B2 9/2014 Rogers et al.
8,845,593 B2 9/2014 Anderson et al.
8,961,475 B2 2/2015 Solomon et al.
8,968,268 B2 3/2015 Anderson et al.
8,999,073 B2 4/2015 Rogers et al.
9,039,989 B2 5/2015 Liu et al.
9,079,692 B2 7/2015 Solomon et al.
9,114,915 B2 8/2015 Solomon et al.
9,186,707 B2 11/2015 Vaillancourt et al.
9,192,449 B2 11/2015 Kerr et al.
9,259,284 B2 2/2016 Rogers et al.
9,259,535 B2 2/2016 Anderson et al.
9,283,367 B2 3/2016 Hoang et al.
9,283,368 B2 3/2016 Hoang et al.
9,352,140 B2 5/2016 Kerr et al.
9,440,062 B2 9/2016 Adams et al.
9,492,574 B2 11/2016 Rasooly et al.
9,533,136 B2 1/2017 Midgette et al.
9,561,298 B2 2/2017 Ferlic et al.
9,572,904 B2 2/2017 Ferlic
9,592,375 B2 3/2017 Tennican
9,700,676 B2 7/2017 Anderson et al.
9,700,677 B2 7/2017 Anderson et al.
9,700,710 B2 7/2017 Anderson et al.
9,707,308 B2 7/2017 Ferlic et al.
9,707,348 B2 7/2017 Anderson et al.
9,707,349 B2 7/2017 Anderson et al.
9,707,350 B2 7/2017 Anderson et al.
9,737,664 B2 8/2017 Gardner et al.
9,809,355 B2 11/2017 Solomon et al.
9,867,975 B2 1/2018 Gardner et al.
9,895,526 B2 2/2018 Korogi et al.
9,907,617 B2 3/2018 Rogers
9,943,676 B2 4/2018 Tekeste
9,999,471 B2 6/2018 Rogers et al.
10,016,587 B2 7/2018 Gardner et al.
10,022,530 B2 7/2018 Tekeste
10,029,087 B2 7/2018 Daneluzzi
10,046,156 B2 8/2018 Gardner
10,099,048 B2 10/2018 Chiu et al.
D834,187 S 11/2018 Ryan
10,155,056 B2 12/2018 Solomon et al.
10,159,828 B2 12/2018 Hoang et al.
10,166,085 B2 1/2019 Ready et al.
10,166,339 B2 1/2019 Solomon et al.
10,166,381 B2 1/2019 Gardner et al.
10,195,000 B2 2/2019 Rogers et al.
10,300,176 B2 5/2019 Woo et al.
10,328,207 B2 6/2019 Anderson et al.
10,335,584 B2 7/2019 Hoang et al.
10,335,585 B2 7/2019 Hoang et al.
10,357,579 B2 7/2019 Chiu et al.
10,391,294 B2 8/2019 Drmanovic
10,406,343 B2 9/2019 Hoang et al.
10,493,261 B2 12/2019 Solomon et al.
10,576,173 B2 3/2020 Chiu et al.
10,589,080 B2 3/2020 Hitchcock et al.
10,610,676 B2 4/2020 Drmanovic
10,695,550 B2 6/2020 Gardner et al.
10,744,316 B2 8/2020 Fangrow
10,806,919 B2 10/2020 Gardner et al.
10,821,278 B2 11/2020 Gardner
10,828,484 B2 11/2020 Bedoe et al.
10,850,085 B2 12/2020 Tekeste
11,331,464 B2 5/2022 Hoang et al.
11,464,962 B2 10/2022 Bedoe et al.
11,497,904 B2 11/2022 Fangrow
2004/0028877 A1 2/2004 Itoh et al.
2005/0013836 A1 1/2005 Raad
2005/0147525 A1 7/2005 Bousquet

(56) References Cited

U.S. PATENT DOCUMENTS

| | | | | |
|---|---|---|---|---|
| 2008/0033371 | A1 | 2/2008 | Updegraff et al. | |
| 2008/0039803 | A1 | 2/2008 | Lynn | |
| 2008/0235888 | A1 | 10/2008 | Vaillancourt et al. | |
| 2009/0028750 | A1 | 1/2009 | Ryan | |
| 2009/0099529 | A1 | 4/2009 | Anderson et al. | |
| 2009/0137969 | A1 | 5/2009 | Colantonio et al. | |
| 2010/0003067 | A1 | 1/2010 | Shaw et al. | |
| 2010/0306938 | A1 | 12/2010 | Rogers et al. | |
| 2011/0064512 | A1 | 3/2011 | Shaw et al. | |
| 2011/0232020 | A1 | 9/2011 | Rogers et al. | |
| 2011/0265825 | A1 | 11/2011 | Rogers et al. | |
| 2011/0296586 | A1 | 12/2011 | Jaros | |
| 2011/0314619 | A1 | 12/2011 | Schweikert | |
| 2012/0042466 | A1 | 2/2012 | Colantonio et al. | |
| 2012/0109073 | A1 | 5/2012 | Anderson et al. | |
| 2012/0216359 | A1 | 8/2012 | Rogers et al. | |
| 2012/0216360 | A1 | 8/2012 | Rogers et al. | |
| 2012/0245531 | A9 | 9/2012 | Anderson et al. | |
| 2012/0296284 | A1 | 11/2012 | Anderson et al. | |
| 2013/0006194 | A1 | 1/2013 | Anderson et al. | |
| 2013/0035667 | A1 | 2/2013 | Anderson et al. | |
| 2013/0171030 | A1 | 7/2013 | Ferlic et al. | |
| 2013/0178804 | A1 | 7/2013 | Tennican | |
| 2014/0135710 | A1 | 5/2014 | Hoang et al. | |
| 2014/0135711 | A1 | 5/2014 | Hoang et al. | |
| 2014/0155868 | A1 | 6/2014 | Nelson et al. | |
| 2014/0248182 | A1 | 9/2014 | Solomon et al. | |
| 2014/0261558 | A1 | 9/2014 | Rogers et al. | |
| 2014/0261581 | A1 | 9/2014 | Rogers et al. | |
| 2014/0276449 | A1 | 9/2014 | Charles et al. | |
| 2014/0322075 | A1 | 10/2014 | Ferlic et al. | |
| 2014/0366914 | A1 | 12/2014 | Kerr et al. | |
| 2015/0000061 | A1 | 1/2015 | Rogers et al. | |
| 2015/0000062 | A1 | 1/2015 | Rogers et al. | |
| 2015/0018774 | A1 | 1/2015 | Anderson et al. | |
| 2015/0114967 | A1* | 4/2015 | Brandriff | B65D 41/045 220/315 |
| 2015/0217106 | A1 | 8/2015 | Banik et al. | |
| 2016/0045629 | A1* | 2/2016 | Gardner | A61B 90/70 422/292 |
| 2016/0088995 | A1* | 3/2016 | Ueda | A61M 39/20 604/256 |
| 2016/0101273 | A1 | 4/2016 | Unger et al. | |
| 2016/0325089 | A1* | 11/2016 | Burkholz | A61M 5/001 |
| 2018/0256879 | A1* | 9/2018 | Chiu | B08B 9/023 |
| 2019/0209781 | A1 | 7/2019 | Solomon et al. | |
| 2020/0121858 | A1 | 4/2020 | Anderson et al. | |
| 2020/0330741 | A1 | 10/2020 | Fangrow | |
| 2021/0001110 | A1 | 1/2021 | Bedoe et al. | |
| 2021/0046302 | A1 | 2/2021 | Dombrowski et al. | |
| 2021/0162194 | A1 | 6/2021 | Gardner et al. | |
| 2021/0170157 | A1 | 6/2021 | Grant et al. | |
| 2021/0244933 | A1* | 8/2021 | Jiang | A61M 39/162 |
| 2021/0353927 | A1 | 11/2021 | Bedoe et al. | |
| 2021/0353928 | A1 | 11/2021 | Bedoe et al. | |
| 2023/0264862 | A1* | 8/2023 | Frisch | B65D 51/245 215/316 |

FOREIGN PATENT DOCUMENTS

| | | | |
|---|---|---|---|
| AU | 2013100345 | A4 | 4/2013 |
| CA | 2692157 | C | 5/2014 |
| CN | 101801435 | A | 8/2010 |
| CN | 103191511 | B | 8/2016 |
| EP | 2272431 | A2 | 6/2010 |
| EP | 2606930 | B1 | 4/2018 |
| EP | 2167166 | B1 | 4/2020 |
| WO | 205188 | A1 | 1/2002 |
| WO | 2009002474 | A1 | 12/2008 |
| WO | 2013066285 | A1 | 5/2013 |
| WO | 2017220729 | A1 | 12/2017 |

OTHER PUBLICATIONS

International Search Report and Written Opinion; International Patent Application No. PCT/US2016/047863; Medline Industries, Inc.; Bedoe, Scott, et al; dated Nov. 28, 2016.

China National Intellectual Property Administration Search Report; Chinese Patent Application No. 201680060068.6; Medline Industries, Inc.; Bedoe, Scott, et al.; dated Sep. 17, 2021.

* cited by examiner

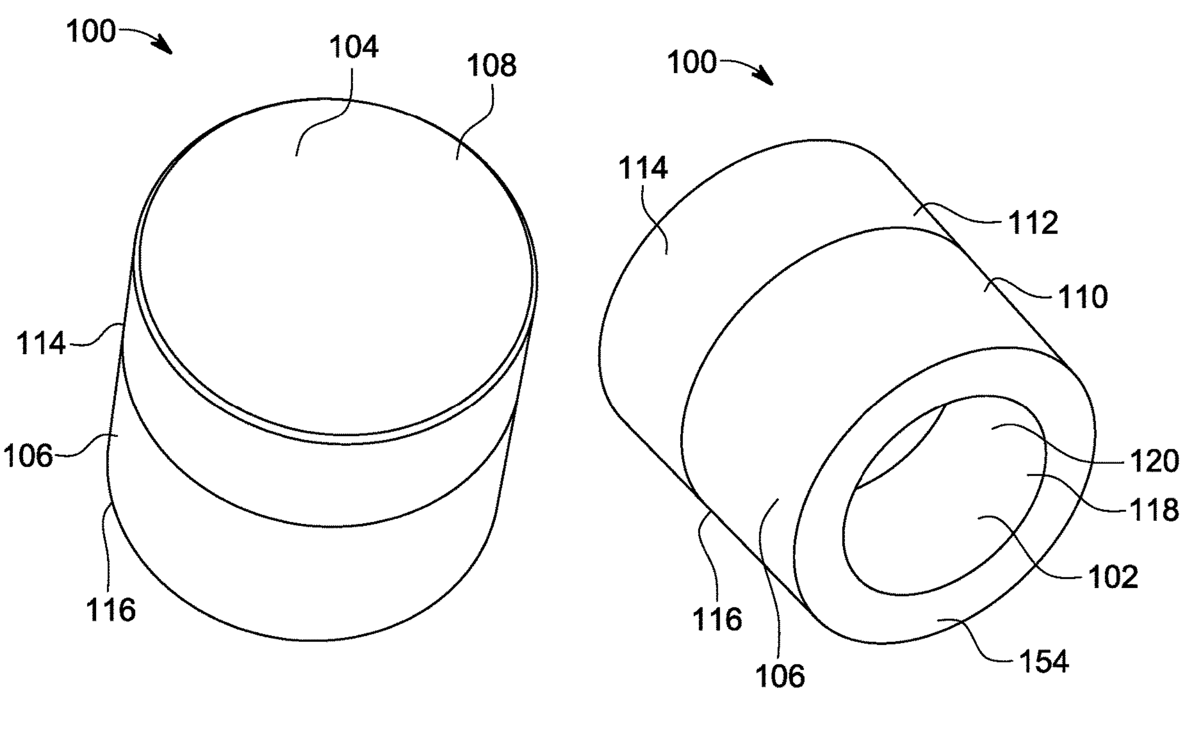
FIG. 1
FIG. 2
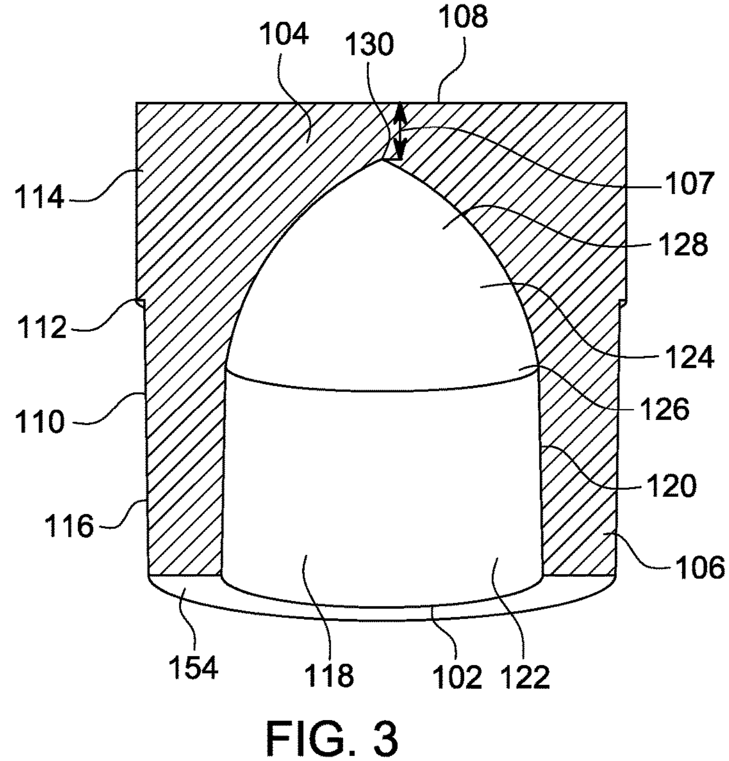
FIG. 3

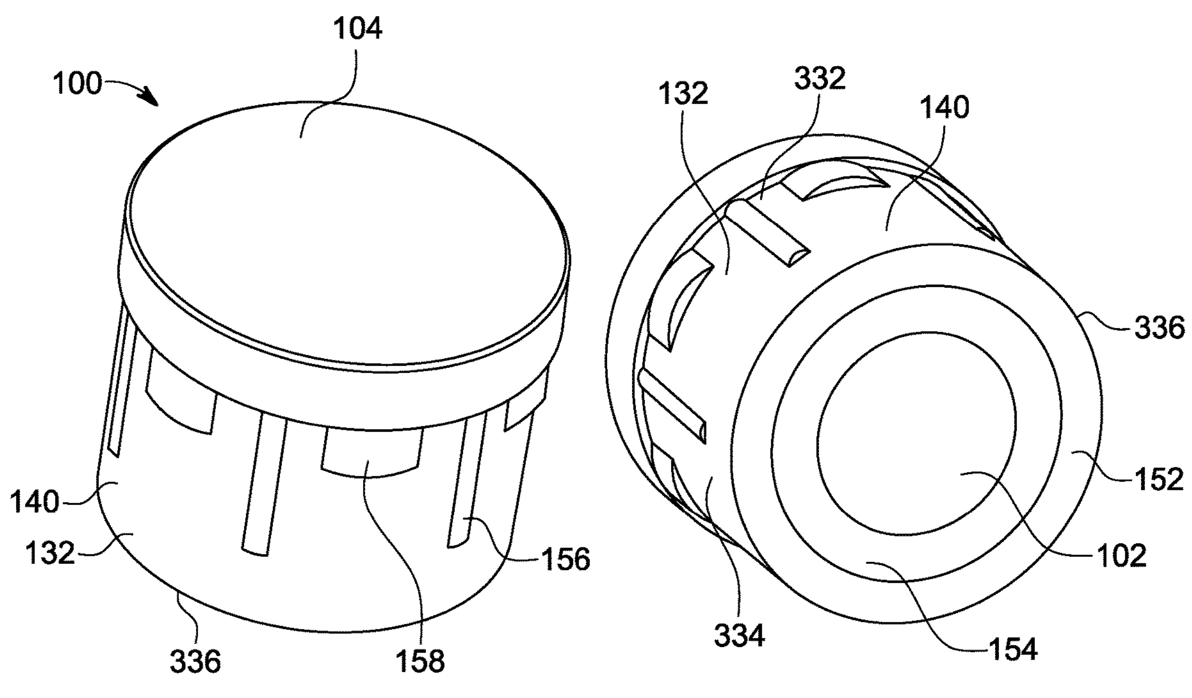
FIG. 4
FIG. 5
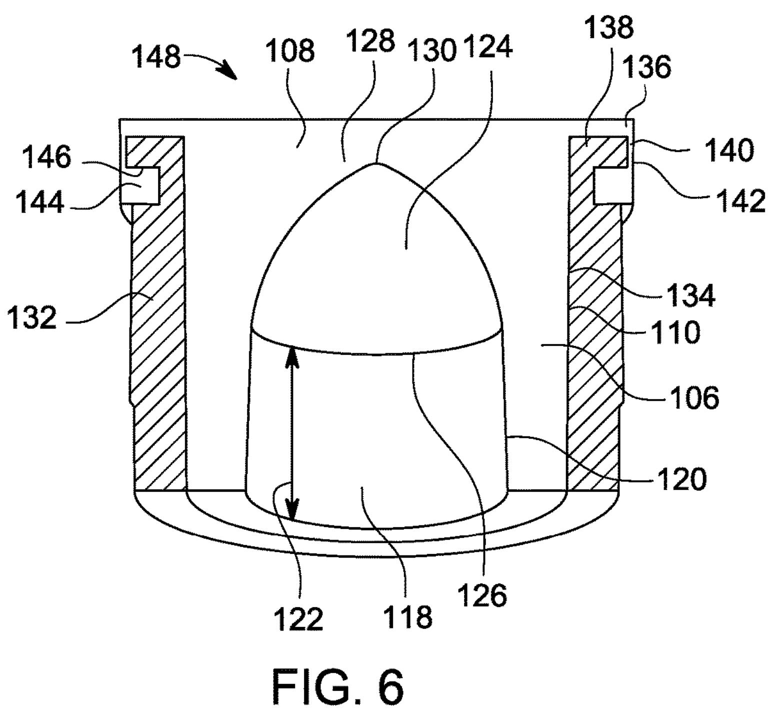
FIG. 6

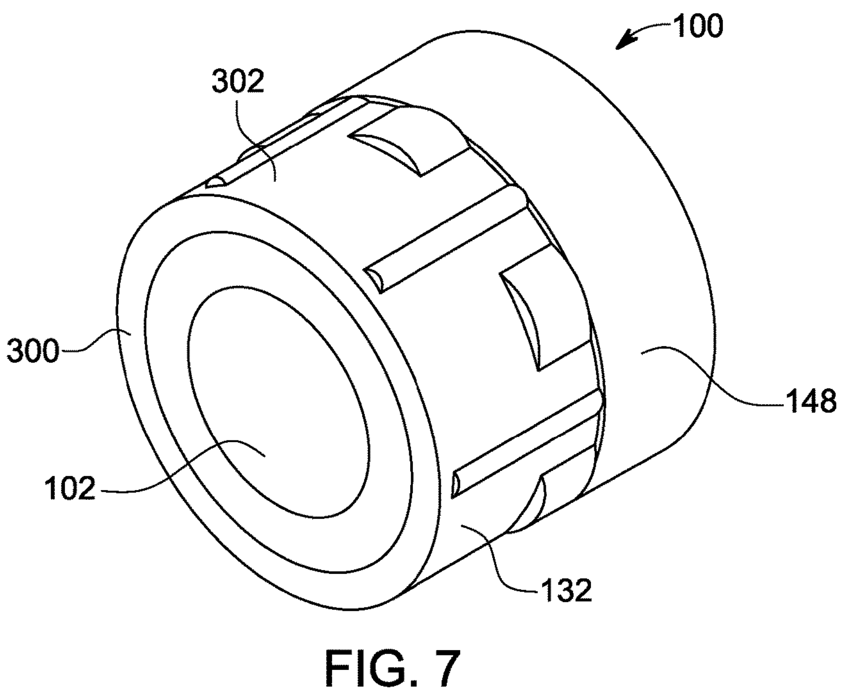
FIG. 7
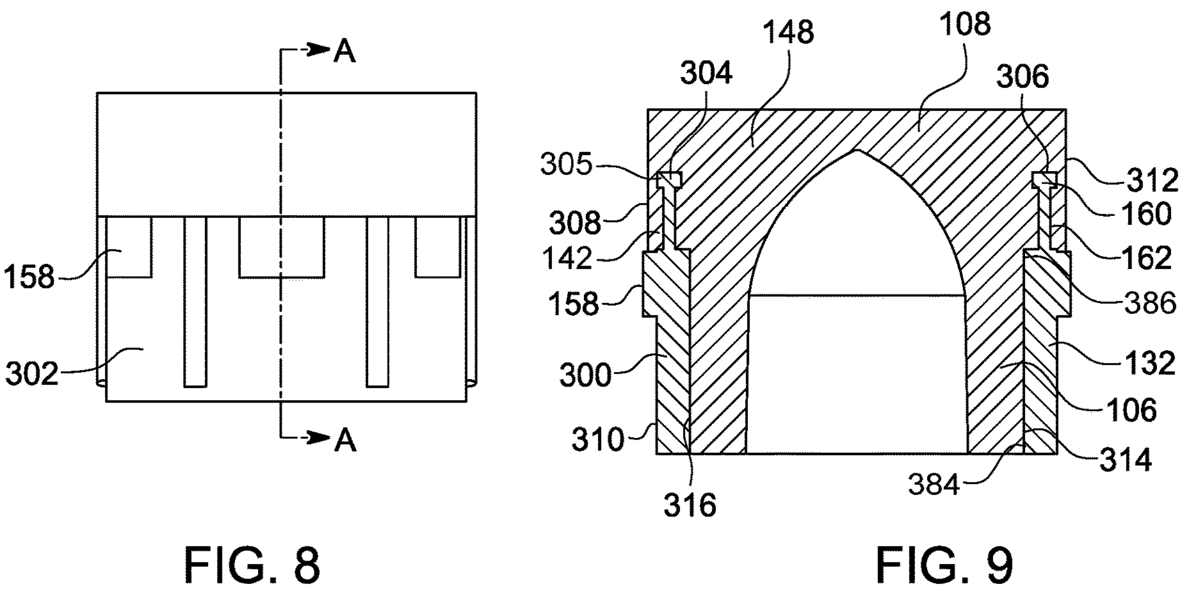
FIG. 8
FIG. 9

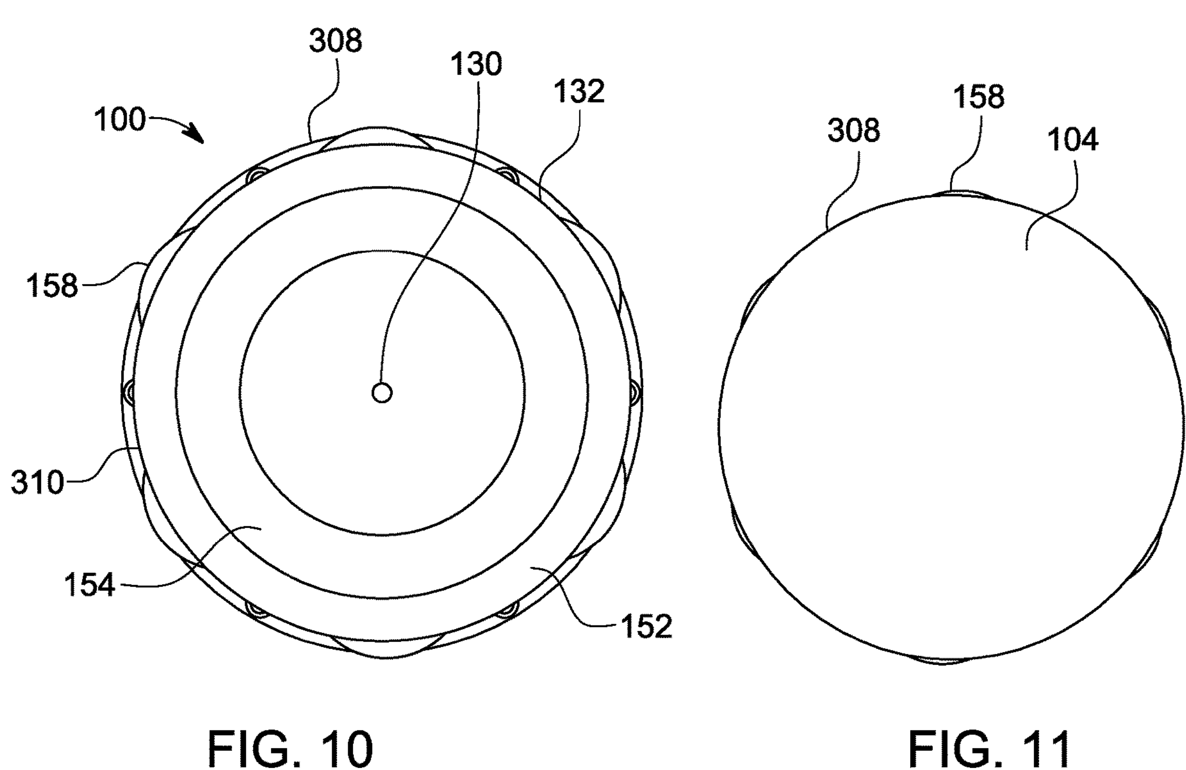
FIG. 10
FIG. 11
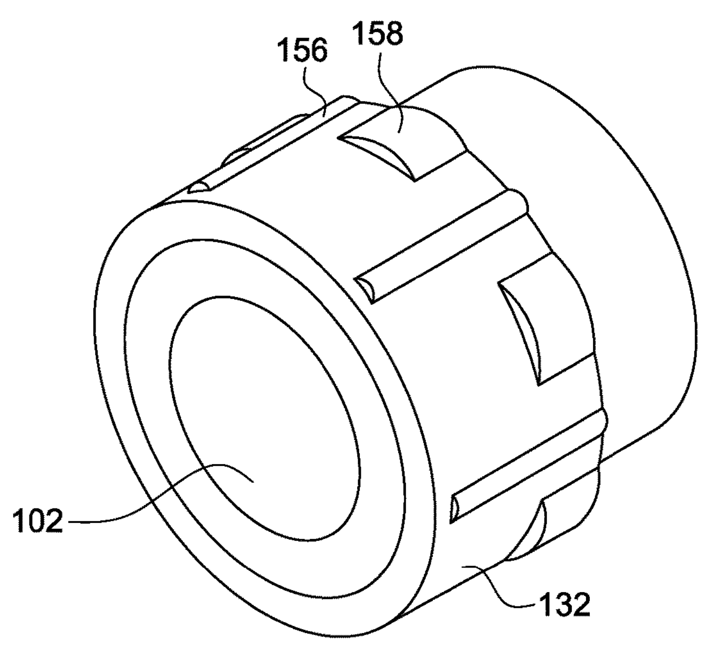
FIG. 12

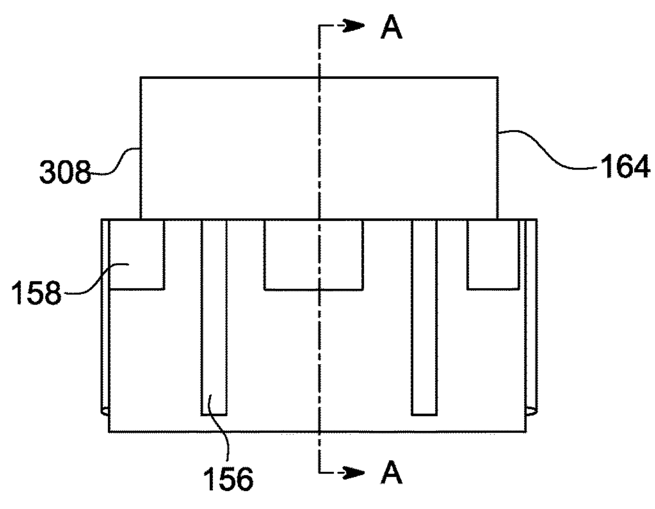
FIG. 13
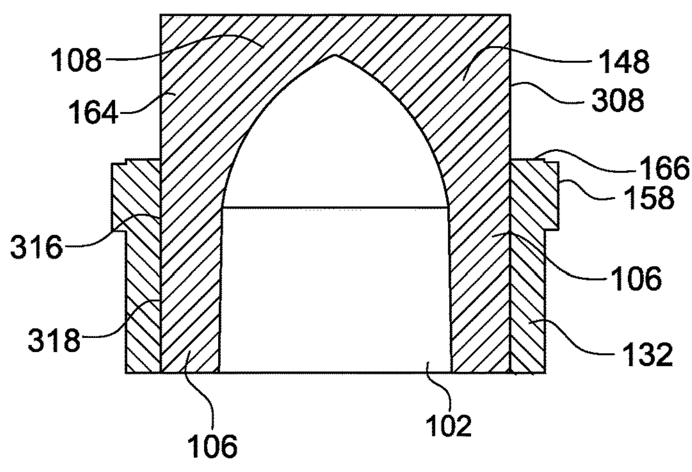
FIG. 14
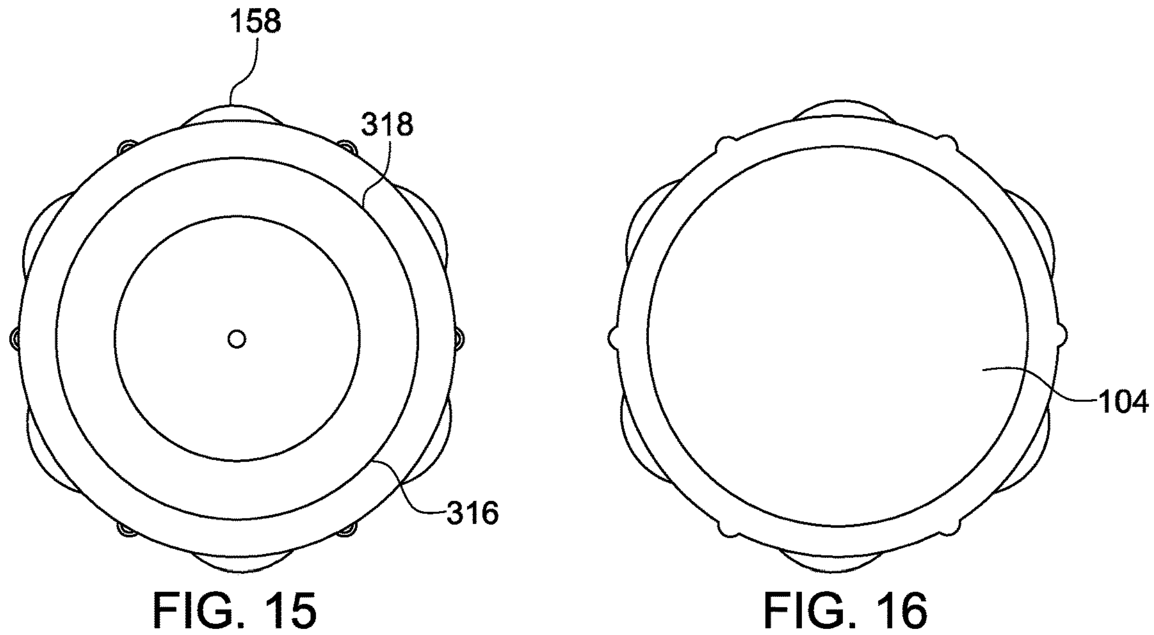
FIG. 15
FIG. 16

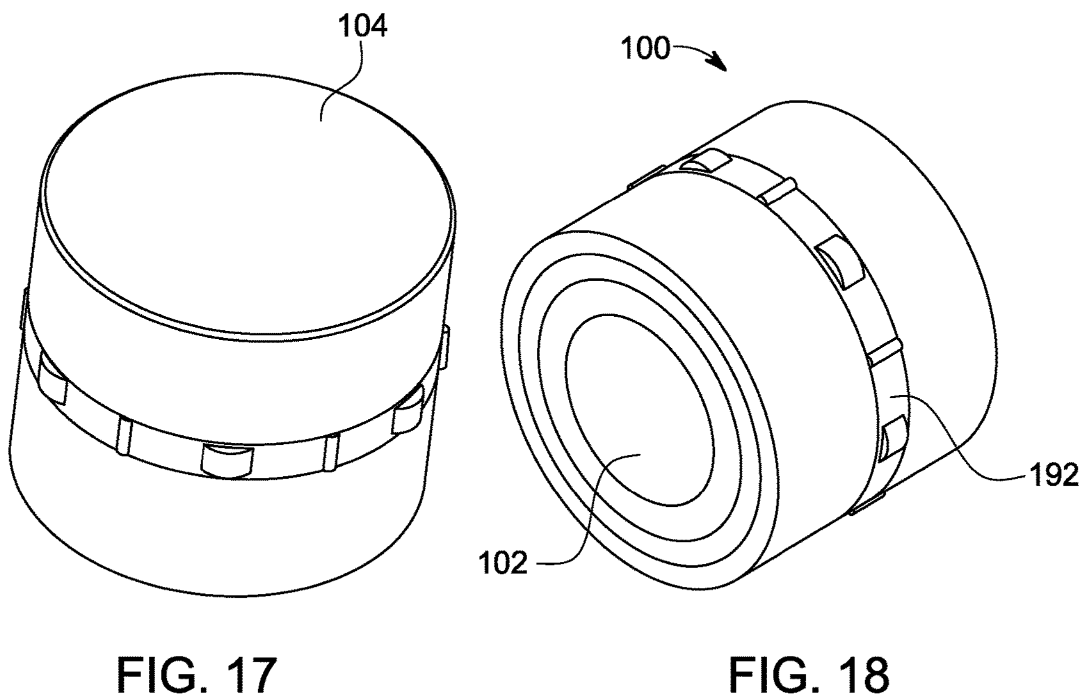
FIG. 17
FIG. 18
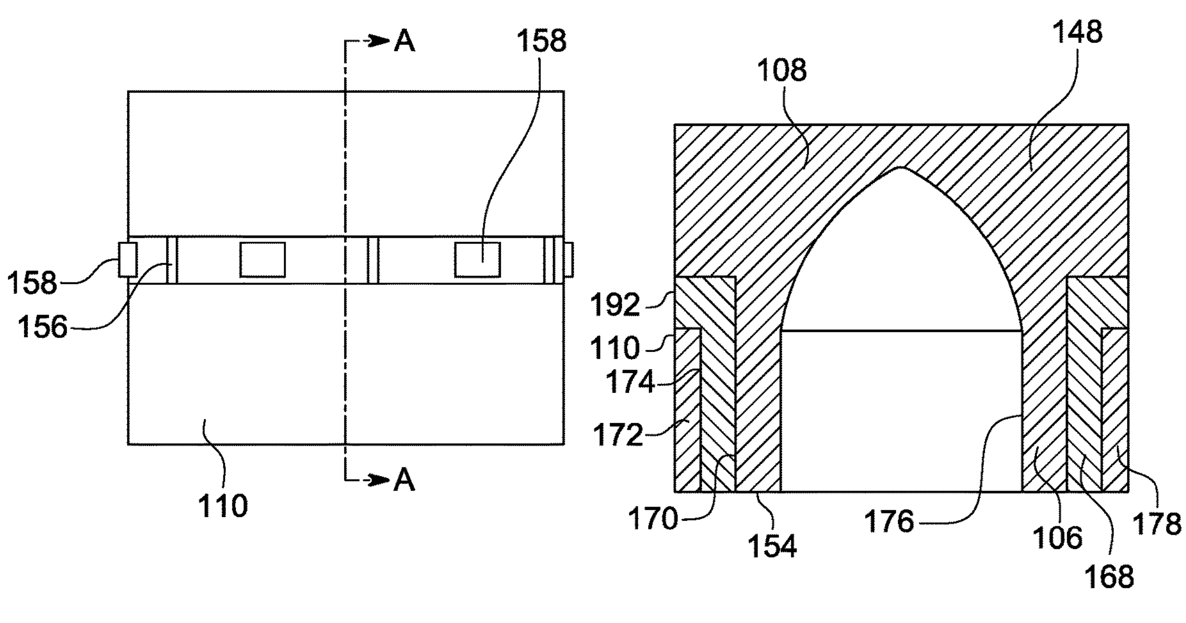
FIG. 19
FIG. 20

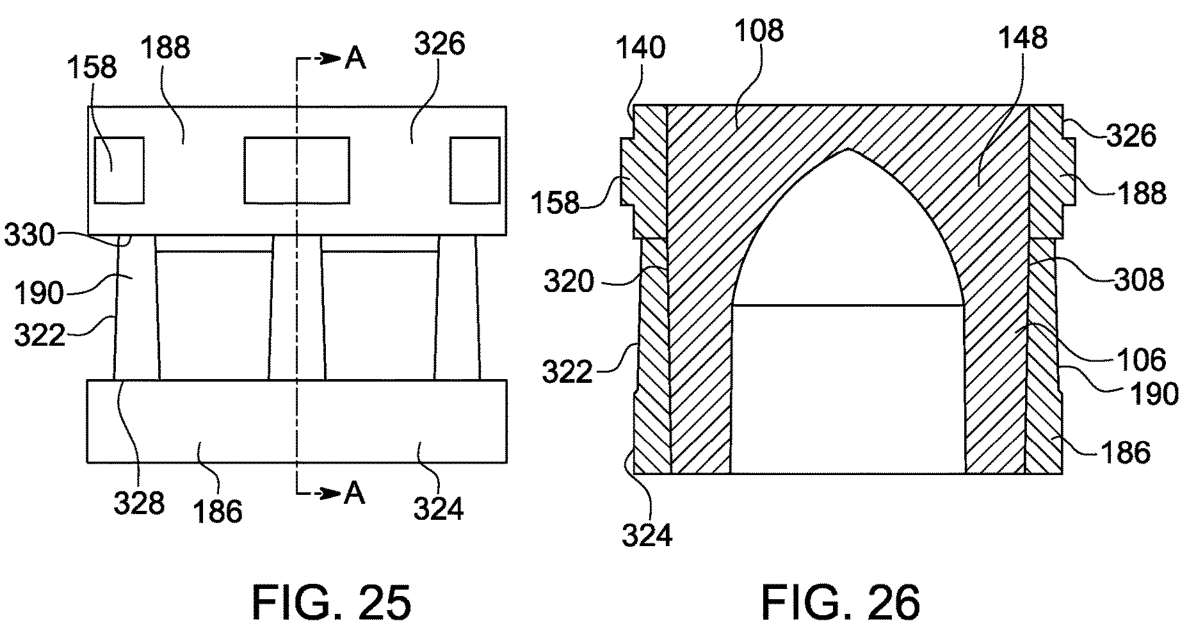
FIG. 25
FIG. 26
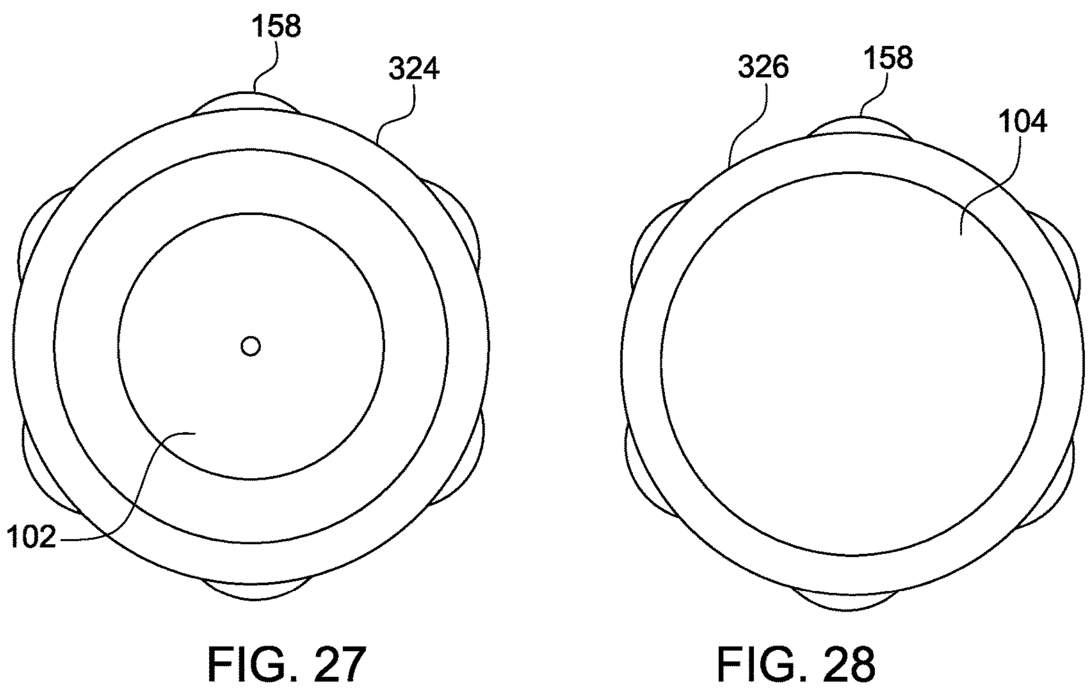
FIG. 27
FIG. 28

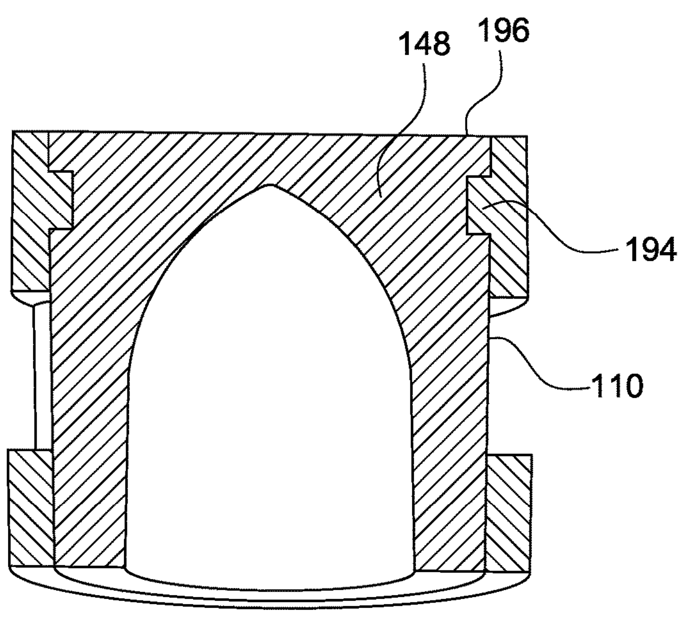
FIG. 29
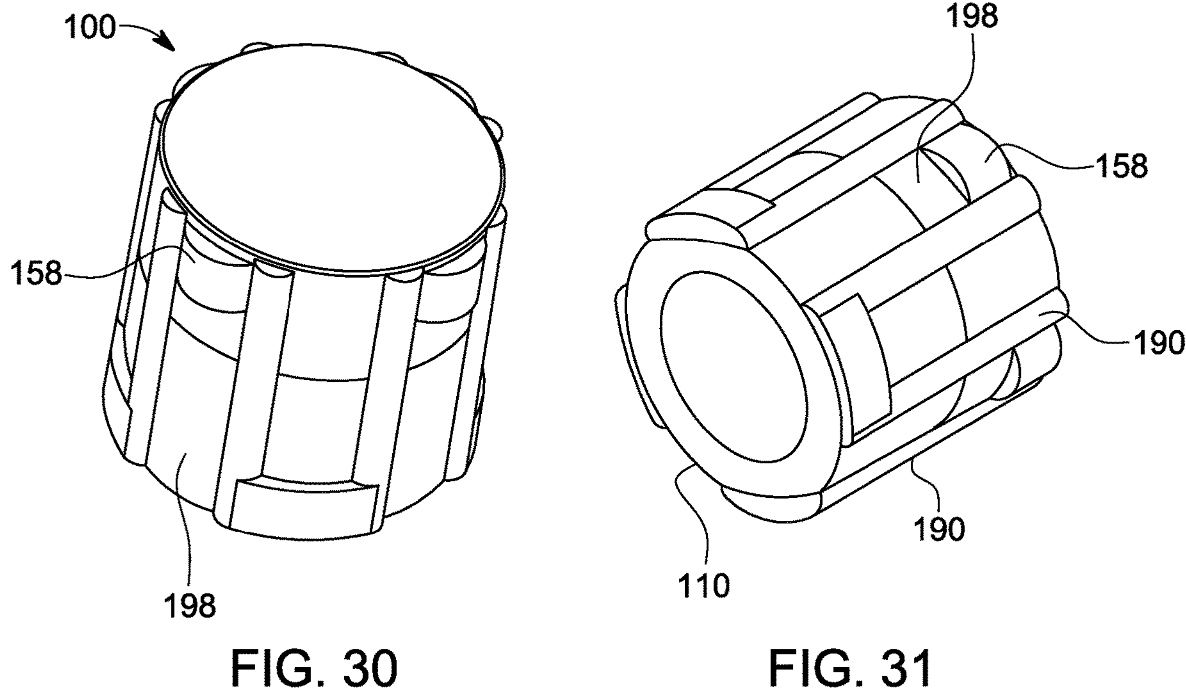
FIG. 30
FIG. 31

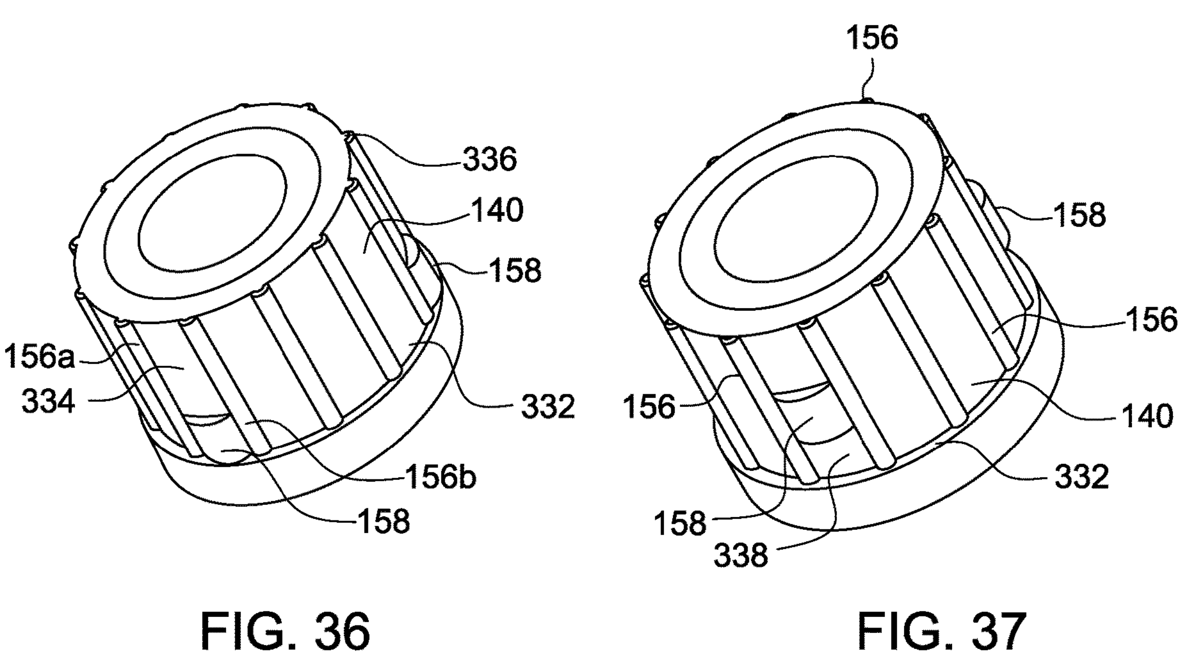
FIG. 36
FIG. 37
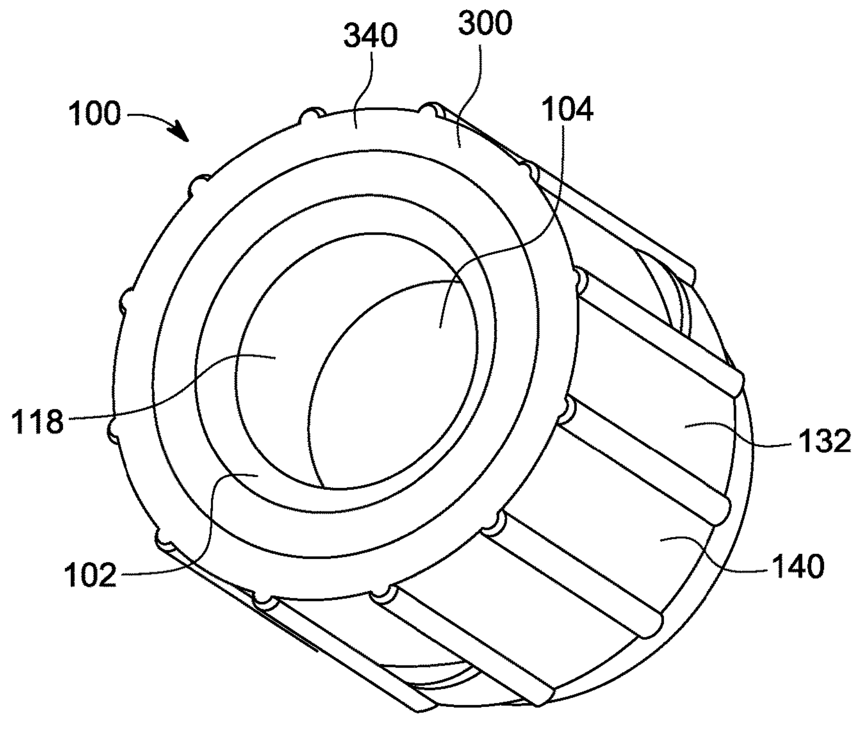
FIG. 38

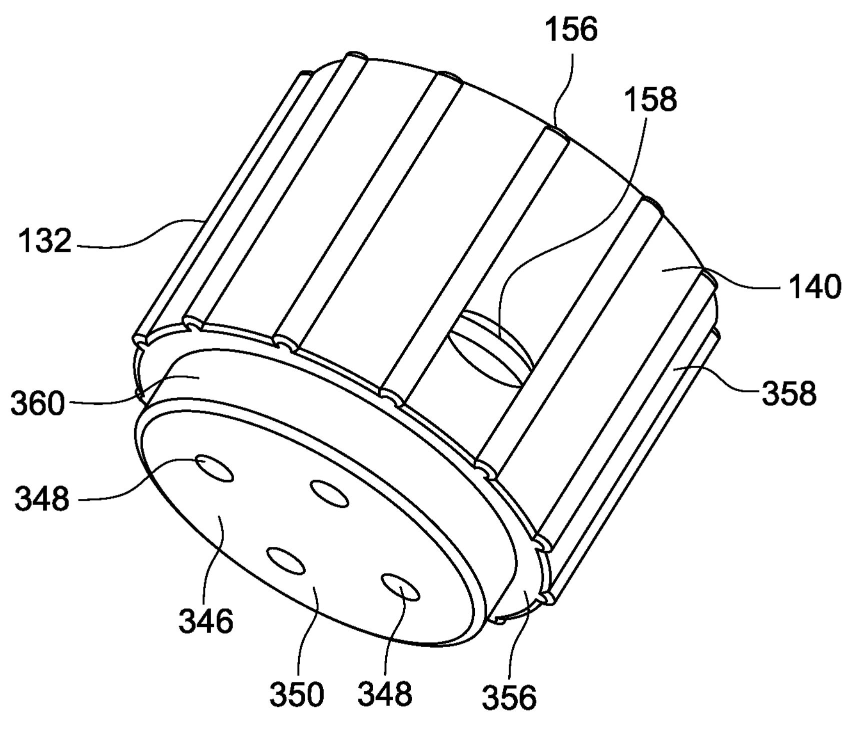
FIG. 39
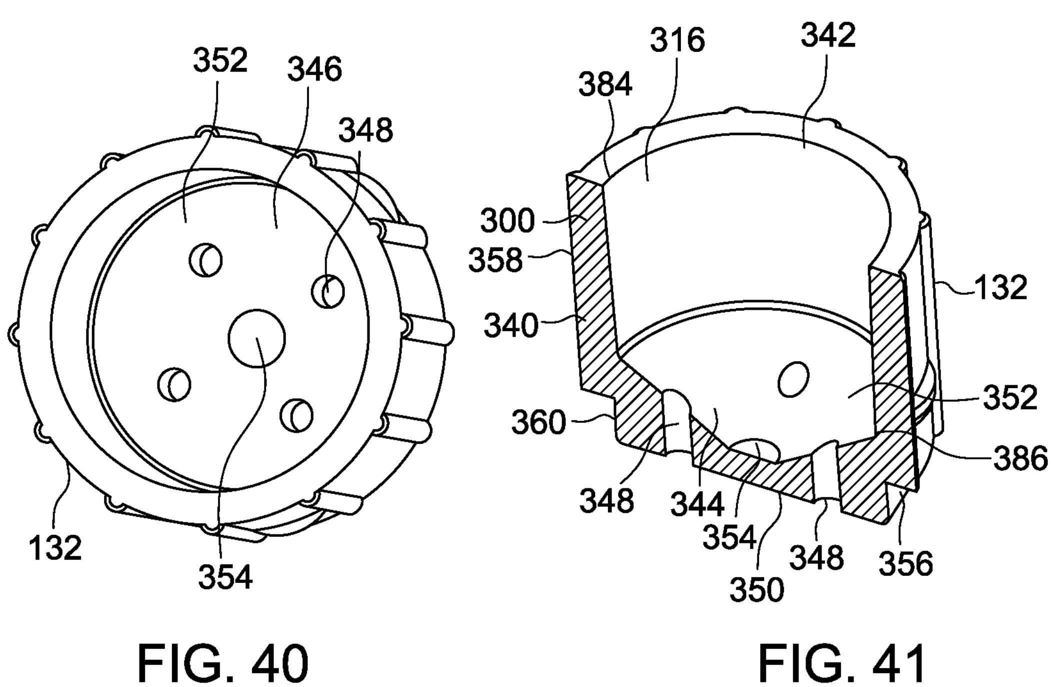
FIG. 40
FIG. 41

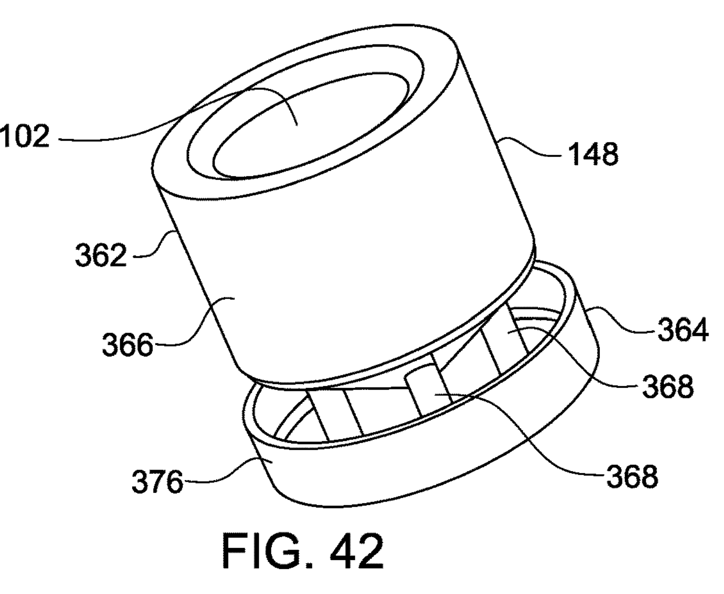
FIG. 42
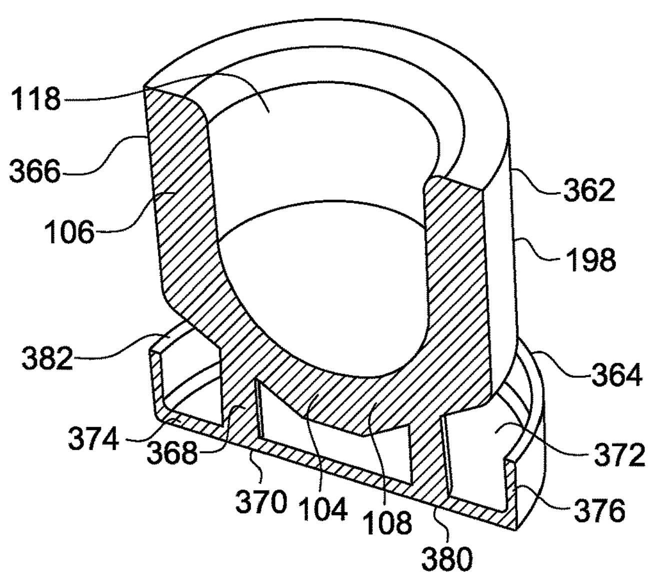
FIG. 43
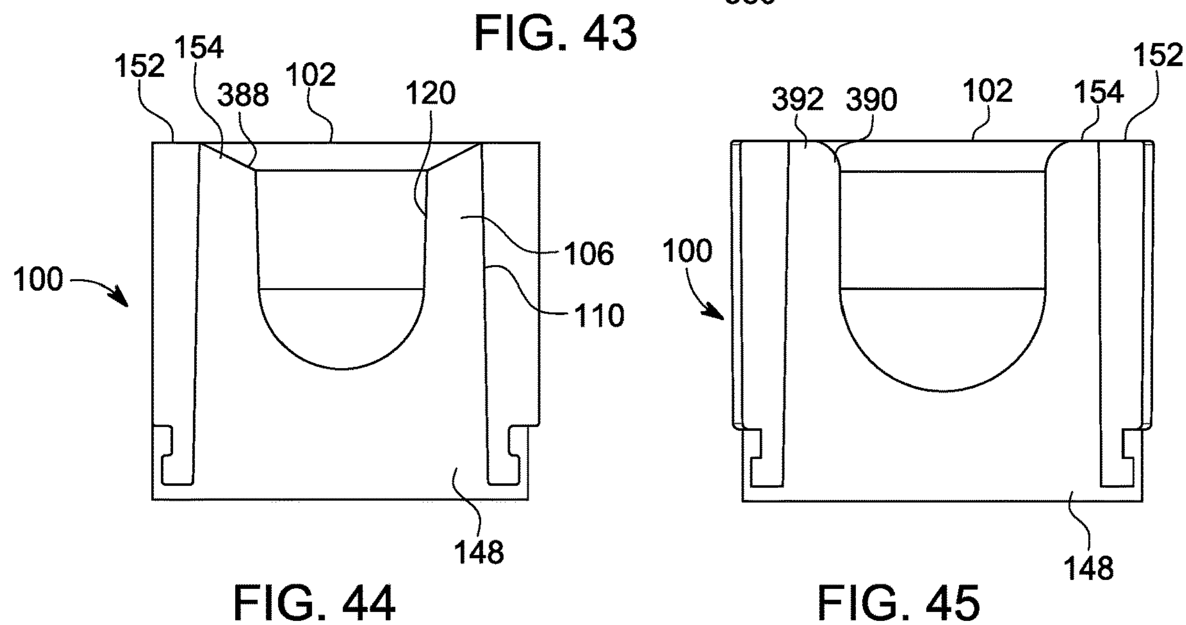
FIG. 44
FIG. 45

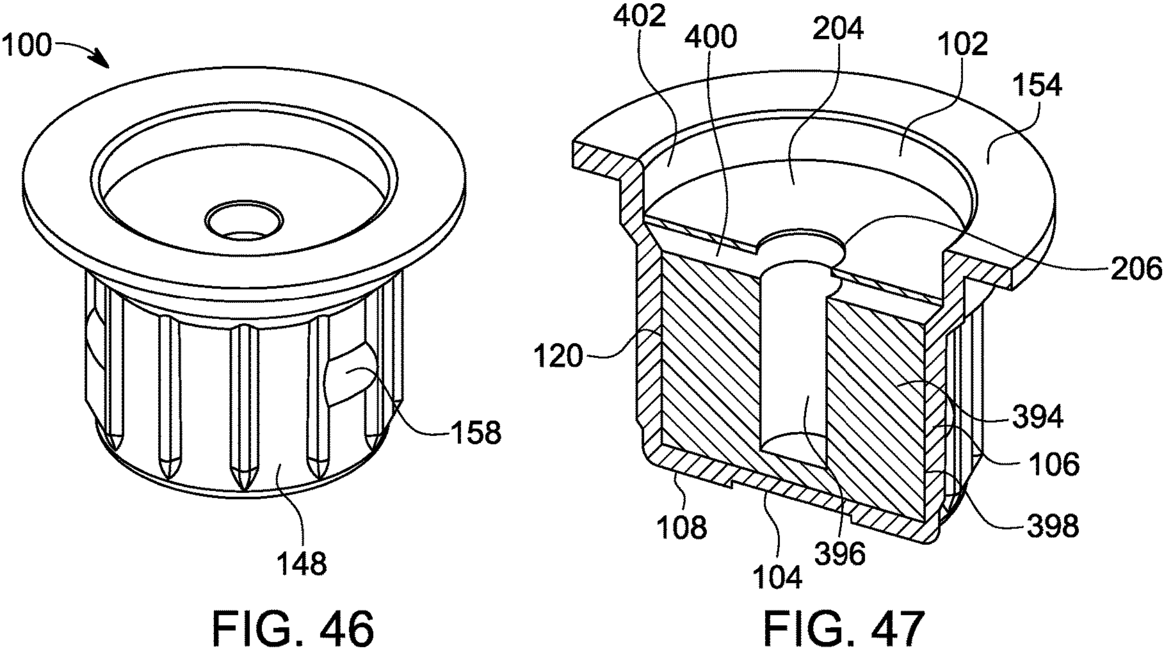
FIG. 46
FIG. 47
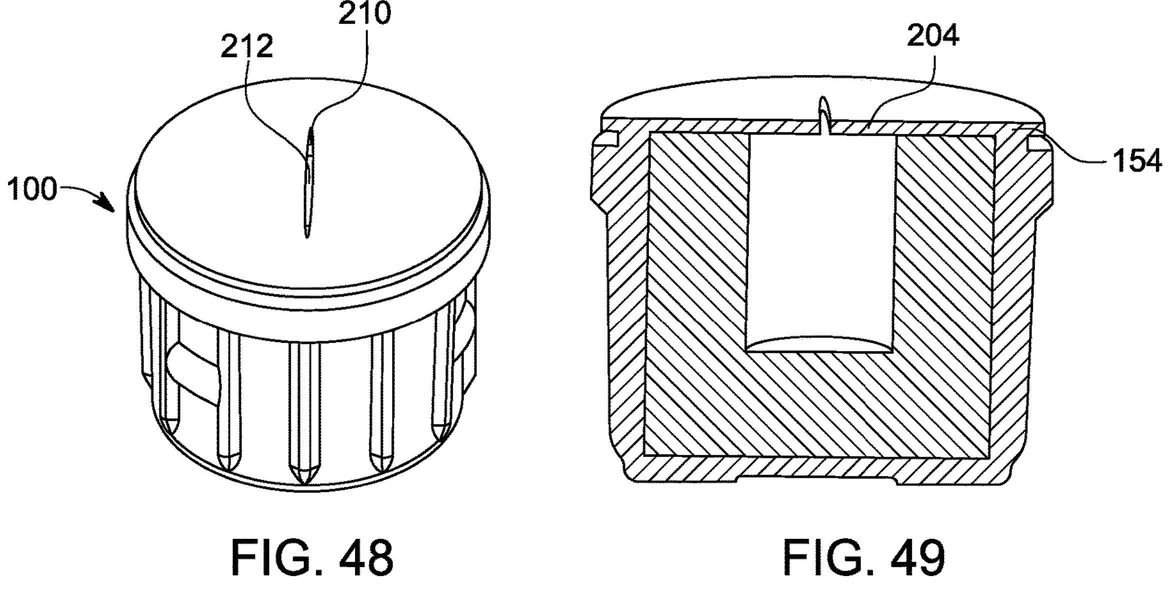
FIG. 48
FIG. 49

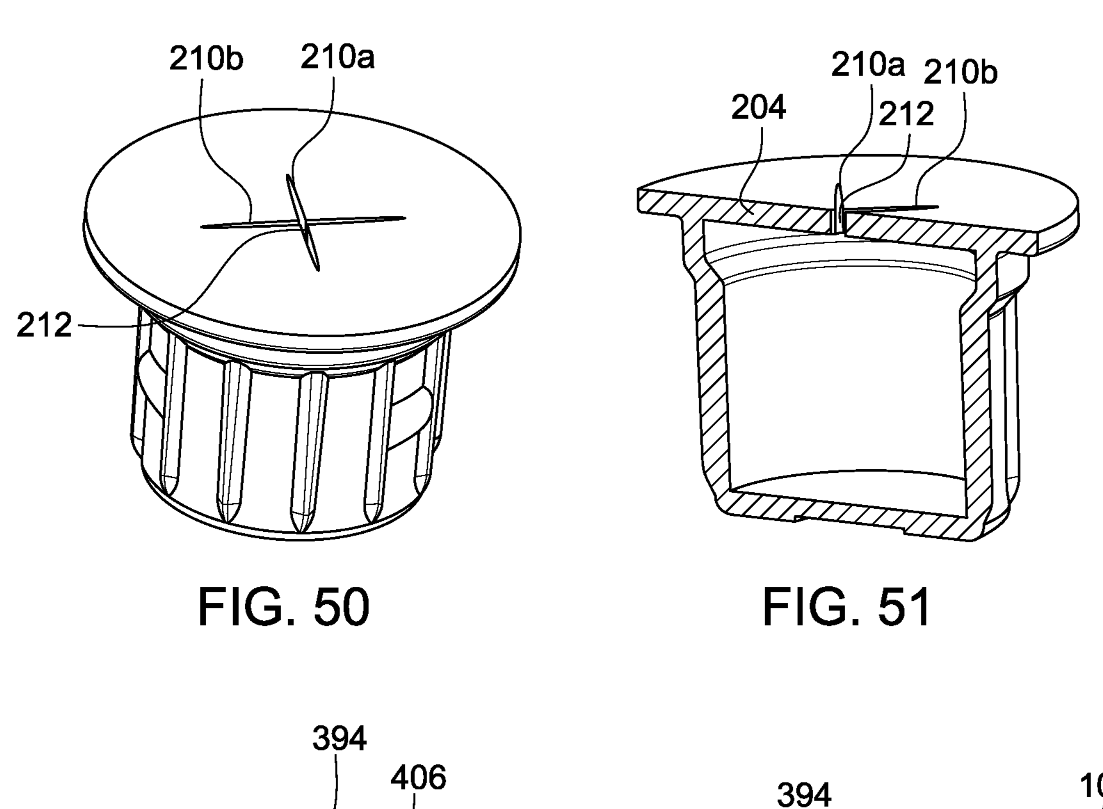
FIG. 50
FIG. 51
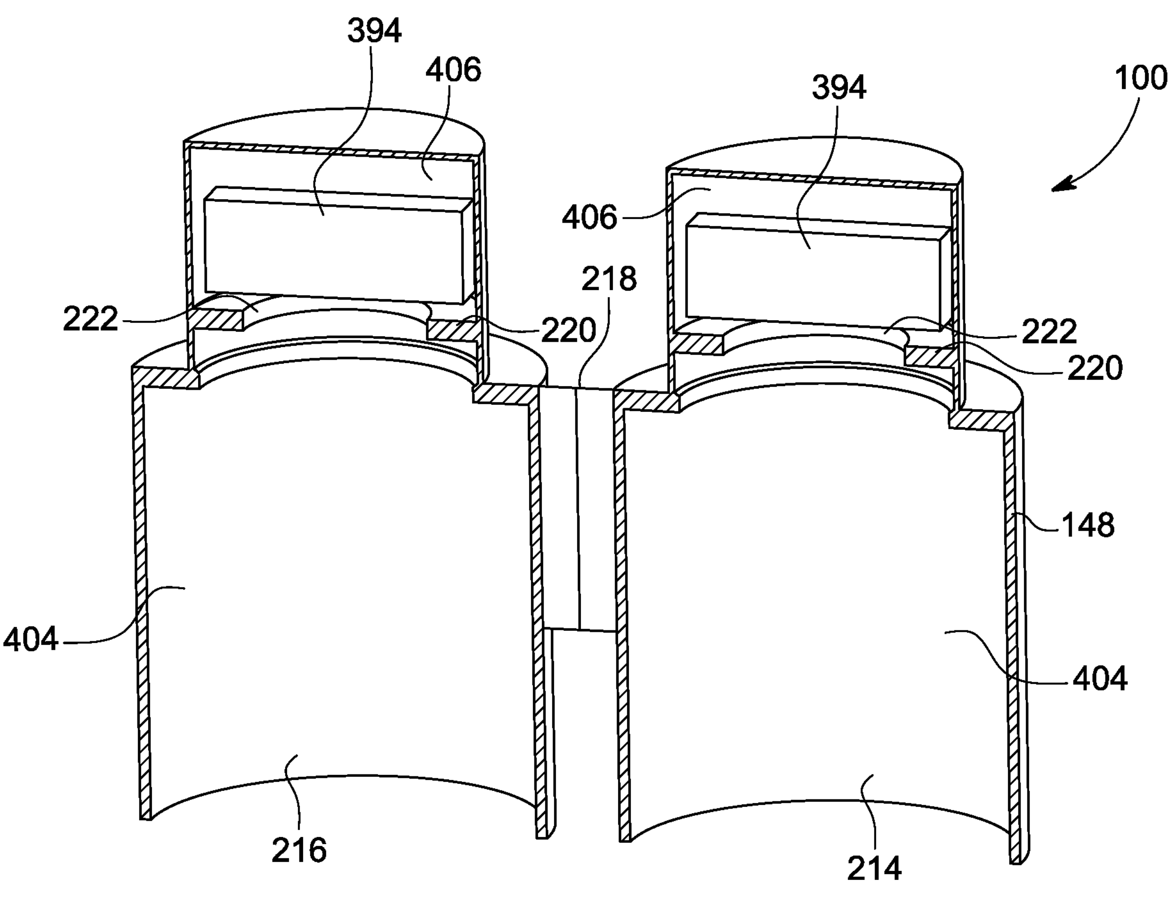
FIG. 52

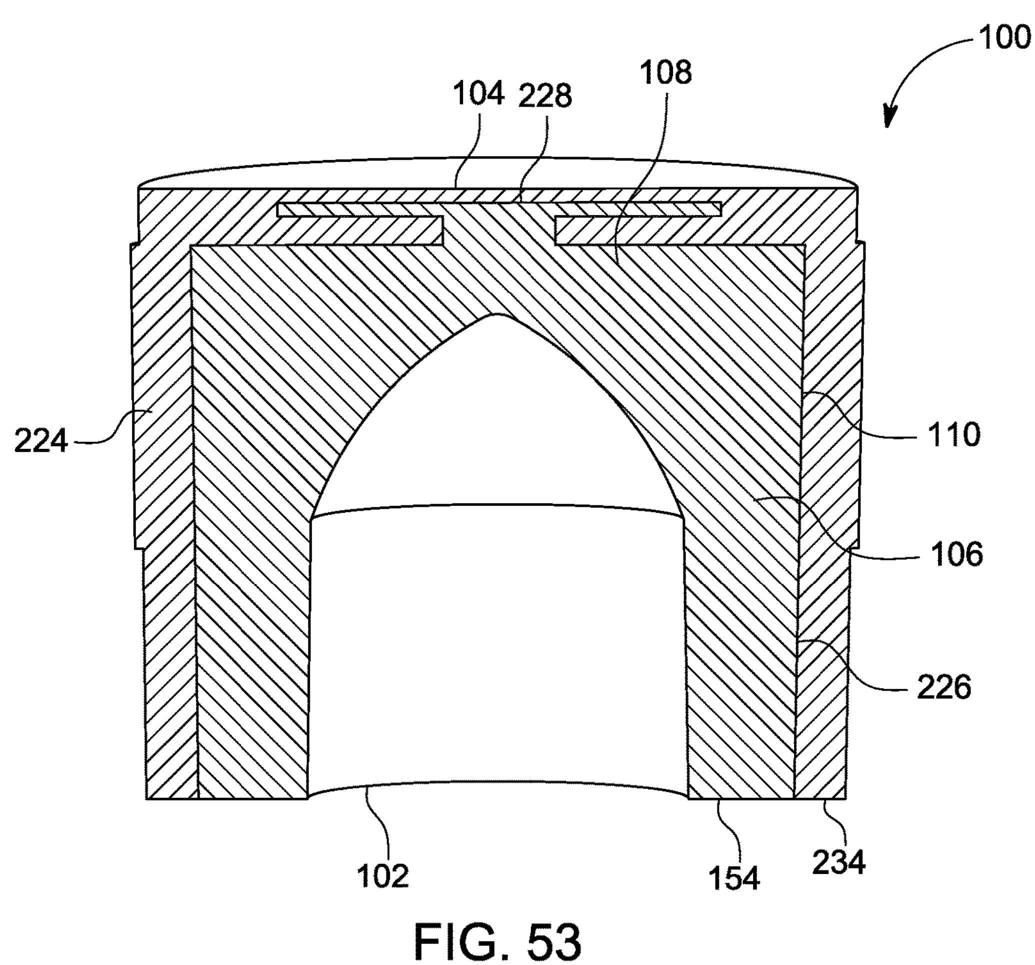
FIG. 53
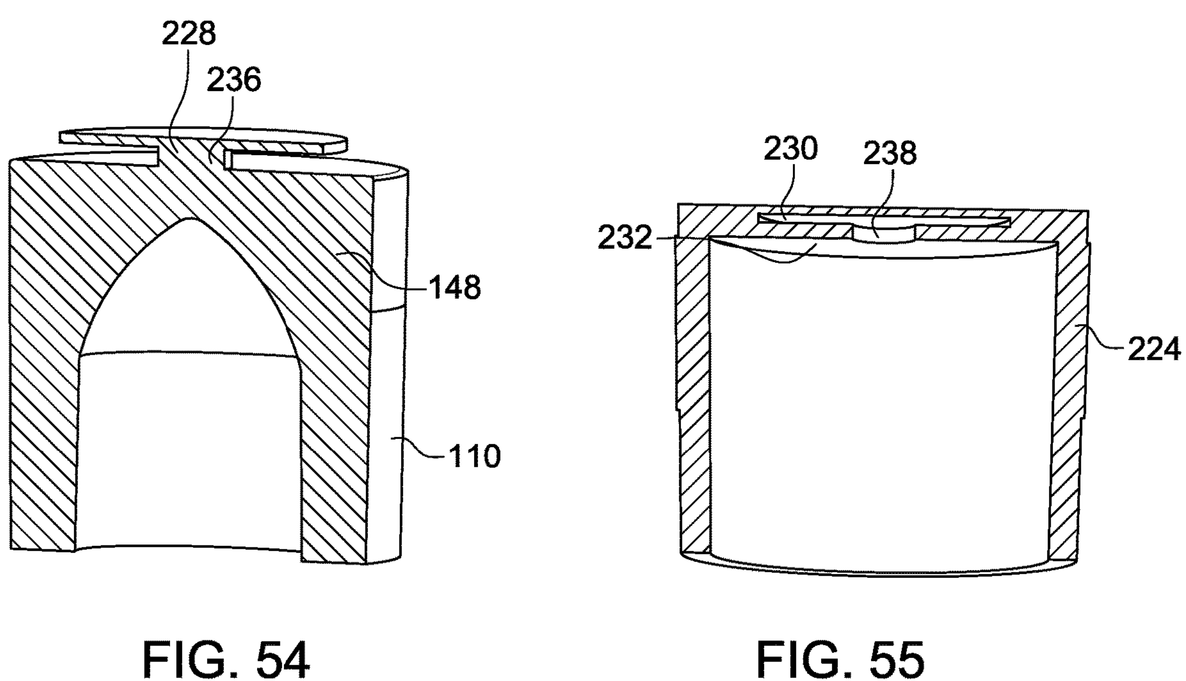
FIG. 54
FIG. 55

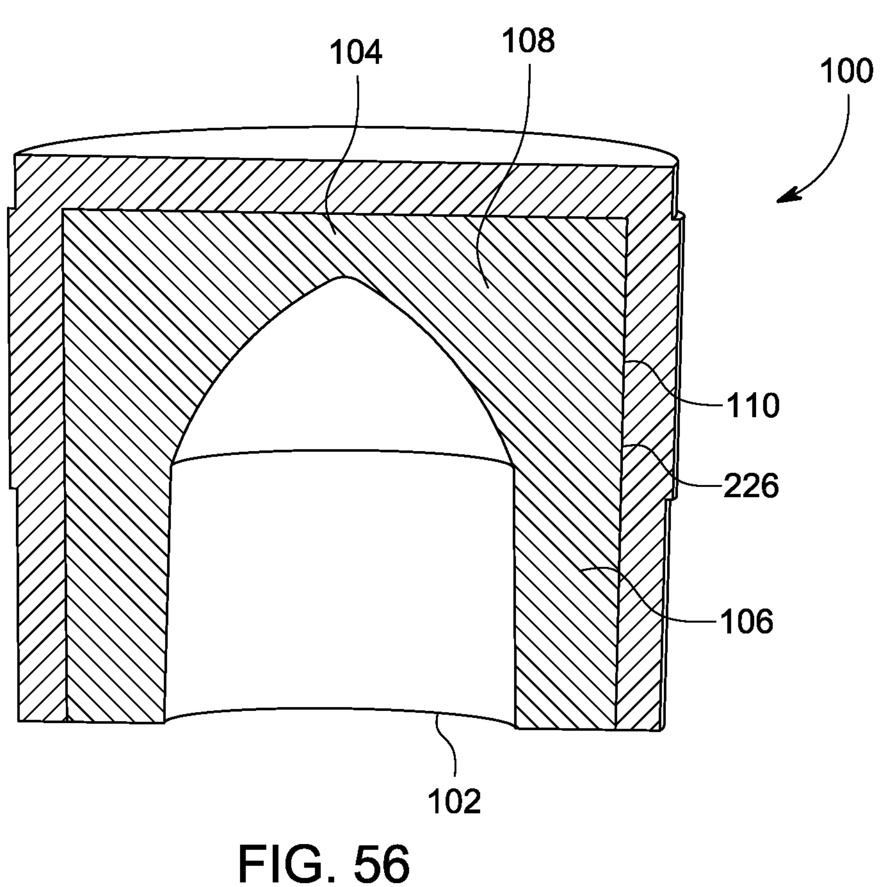
FIG. 56
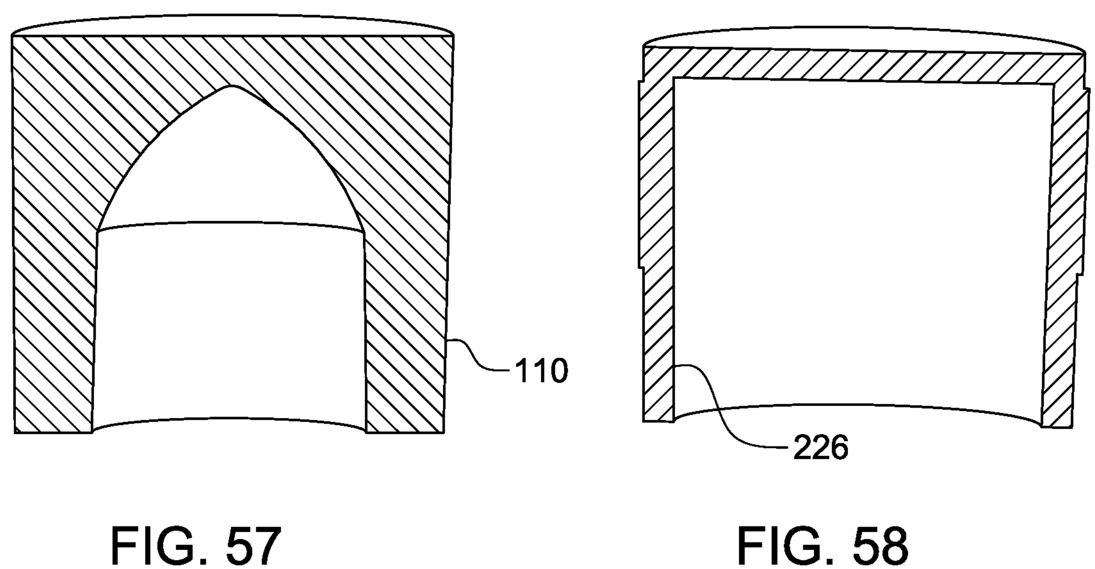
FIG. 57
FIG. 58

156
114
116

130
114
118
116

156
114
106
116
120

130
114
124
414
412
118
116
416
120
106
122

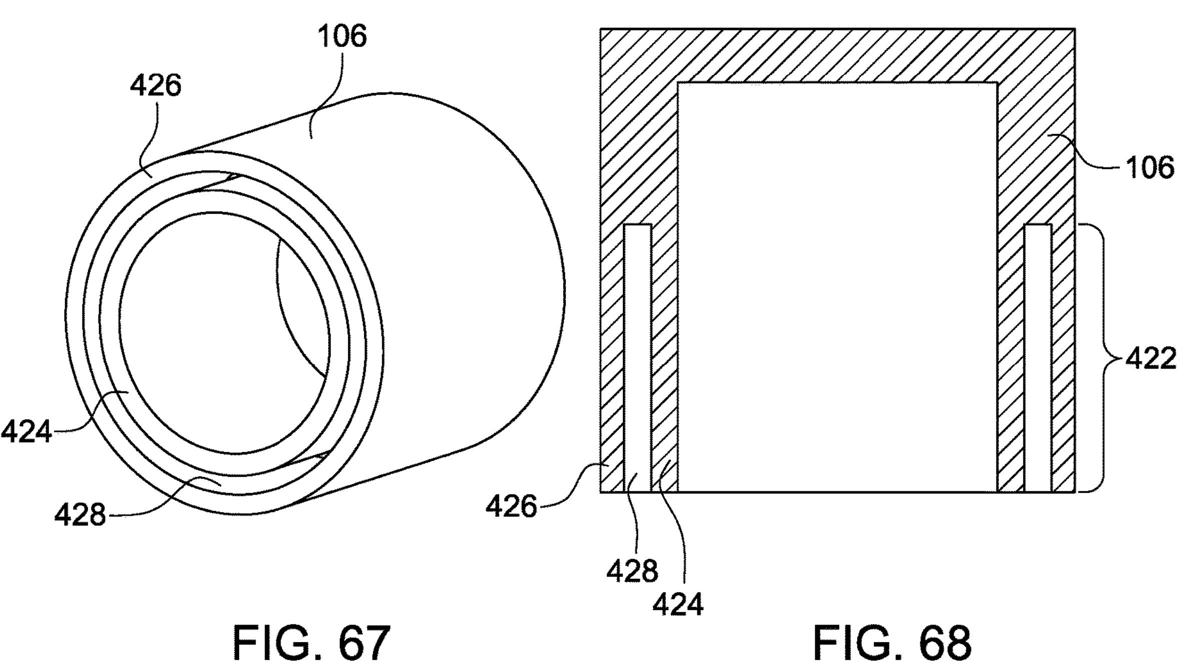
FIG. 67
FIG. 68
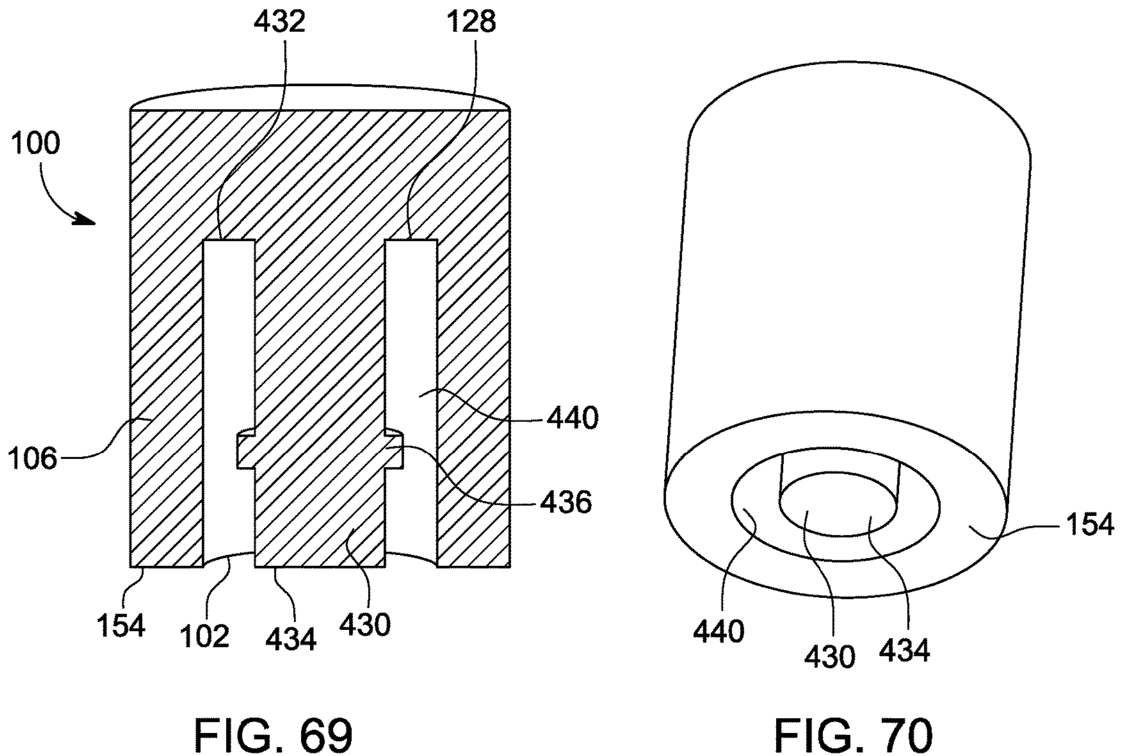
FIG. 69
FIG. 70

DISINFECTING CAP

BACKGROUND

Within the medical field, and in particular the area of infusion of fluids or aspiration of fluids to or from a patient, there is a need to prevent the transmission of pathogens into or onto a patient from a potentially contaminated surface of a medical implement. Such pathogens include microorganisms such as bacteria and viruses. The transmission of pathogens into a patient may result in an infection that could be life threatening. Common sites for such transmissions are found at access "sites" of medical implements such as a luer port, vial, needle free valve, or an injection port of a vessel, tubing, or catheter. Even non-intrusive medical implements such as stethoscopes or otoscopes can transmit pathogens to a patient.

Accordingly, a need exists for an apparatus and technique for cleaning a site on a medical implement prior to contact with a patient.

BRIEF DESCRIPTION OF THE DRAWINGS

Advantages of the invention will become apparent upon reading the following detailed description and upon reference to the drawings.

FIG. 1 is a perspective view of a disinfecting cap exemplary embodiment showing a closed end of the cap.

FIG. 2 is a perspective view of the disinfecting cap of FIG. 1 showing an open end of the cap.

FIG. 3 shows a cross-sectional view of the disinfecting cap of FIGS. 1-2.

FIG. 4 is a perspective view of a disinfecting cap exemplary embodiment showing a closed end of the cap.

FIG. 5 is a perspective view of the disinfecting cap of FIG. 4 showing an open end of the cap.

FIG. 6 shows a cross-sectional view of the disinfecting cap of FIGS. 4-5.

FIG. 7 is a perspective view of a disinfecting cap exemplary embodiment showing an open end of the cap.

FIG. 8 is a side view of the disinfecting cap of FIG. 7.

FIG. 9 is a cross-sectional view of the disinfecting cap of FIG. 8 along line A-A.

FIG. 10 is an end view of the disinfecting cap of FIG. 7 showing an open end.

FIG. 11 is an end view of the disinfecting cap of FIG. 7 showing a closed end.

FIG. 12 is a perspective view of a disinfecting cap exemplary embodiment showing an open end of the cap.

FIG. 13 is a side view of the disinfecting cap of FIG. 12.

FIG. 14 is a cross-sectional view of the disinfecting cap of FIG. 13 along line A-A.

FIG. 15 is an end view of the disinfecting cap of FIG. 12 showing an open end.

FIG. 16 is an end view of the disinfecting cap of FIG. 12 showing a closed end.

FIG. 17 is a perspective view of a disinfecting cap exemplary embodiment showing a closed end of the cap.

FIG. 18 is a perspective view of the disinfecting cap of FIG. 17 showing an open end of the cap.

FIG. 19 is a side view of the disinfecting cap of FIG. 17.

FIG. 20 is a cross-sectional view of the disinfecting cap of FIG. 19 along line A-A.

FIG. 25 is a side view of the disinfecting cap of FIG. 23.

FIG. 26 is a cross-sectional view of the disinfecting cap of FIG. 25 along line A-A.

FIG. 27 is an end view of the disinfecting cap of FIG. 23 showing an open end.

FIG. 28 is an end view of the disinfecting cap of FIG. 23 showing a closed end.

FIG. 29 is a perspective, cross-sectional view of an alternative embodiment of the disinfecting cap of FIG. 26.

FIG. 30 is a perspective view of a disinfecting cap exemplary embodiment showing a closed end of the cap.

FIG. 31 is a perspective view of the disinfecting cap of FIG. 30 showing an open end of the cap.

FIG. 36 is a perspective view of a disinfecting cap exemplary embodiment showing an open end of the cap.

FIG. 37 is a perspective view of a disinfecting cap exemplary embodiment showing an open end of the cap.

FIG. 38 is a perspective view of a disinfecting cap exemplary embodiment showing an open end of the cap.

FIG. 39 is a perspective view of a skirt of the disinfecting cap of FIG. 38 showing a closed end of the skirt.

FIG. 40 is a perspective view of a skirt of the disinfecting cap of FIG. 38 showing an open end of the skirt.

FIG. 41 is a cross-sectional, perspective view of a skirt of the disinfecting cap of FIG. 38.

FIG. 42 is a perspective view of a cap body of the disinfecting cap of FIG. 38 showing an open end of the body.

FIG. 43 is a cross-sectional, perspective view of a cap body of the disinfecting cap of FIG. 38.

FIG. 44 is a cross-sectional view of a disinfecting cap exemplary embodiment.

FIG. 45 is a cross-sectional view of a disinfecting cap exemplary embodiment.

FIG. 46 is a perspective view of a disinfecting cap exemplary embodiment showing an open end of the cap.

FIG. 47 is a perspective, cross-sectional view of the disinfecting cap of FIG. 46.

FIG. 48 is a perspective view of a disinfecting cap exemplary embodiment showing an open end of the cap.

FIG. 49 is a perspective, cross-sectional view of the disinfecting cap of FIG. 48.

FIG. 50 is a perspective view of a disinfecting cap exemplary embodiment showing an open end of the cap.

FIG. 51 is a perspective, cross-sectional view of the disinfecting cap of FIG. 50.

FIG. 52 is a perspective view of a disinfecting cap exemplary embodiment showing the cap in an open configuration.

FIG. 53 is a perspective, cross-sectional view of a disinfecting cap exemplary embodiment.

FIG. 54 is a perspective, cross-sectional view of a cap body of the disinfecting cap of FIG. 53.

FIG. 55 is a perspective, cross-sectional view of a shell of the disinfecting cap of FIG. 53.

FIG. 56 is a perspective, cross-sectional view of a disinfecting cap exemplary embodiment.

FIG. 57 is a perspective, cross-sectional view of a cap body of the disinfecting cap of FIG. 56.

FIG. 58 is a perspective, cross-sectional view of a shell of the disinfecting cap of FIG. 56.

FIG. 67 is a perspective view of a disinfecting cap exemplary embodiment showing an open end of the cap.

FIG. 68 is a perspective, cross-sectional view of the disinfecting cap of FIG. 67.

FIG. 69 is a perspective, cross-sectional view of disinfecting cap exemplary embodiment.

FIG. 70 is a perspective view of the disinfecting cap of FIG. 69 showing an open end of the cap.

Figures 21, 22:
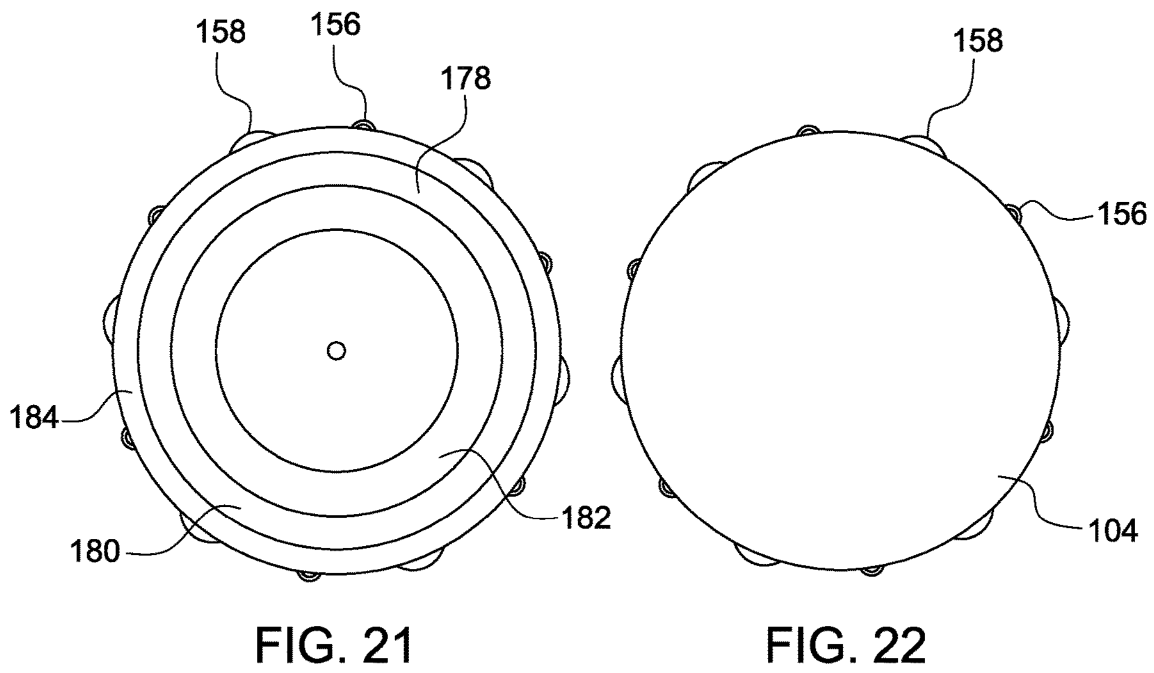
FIG. 21 is an end view of the disinfecting cap of FIG. 17 showing an open end.
FIG. 22 is an end view of the disinfecting cap of FIG. 17 showing a closed end.
Figures 23, 24:
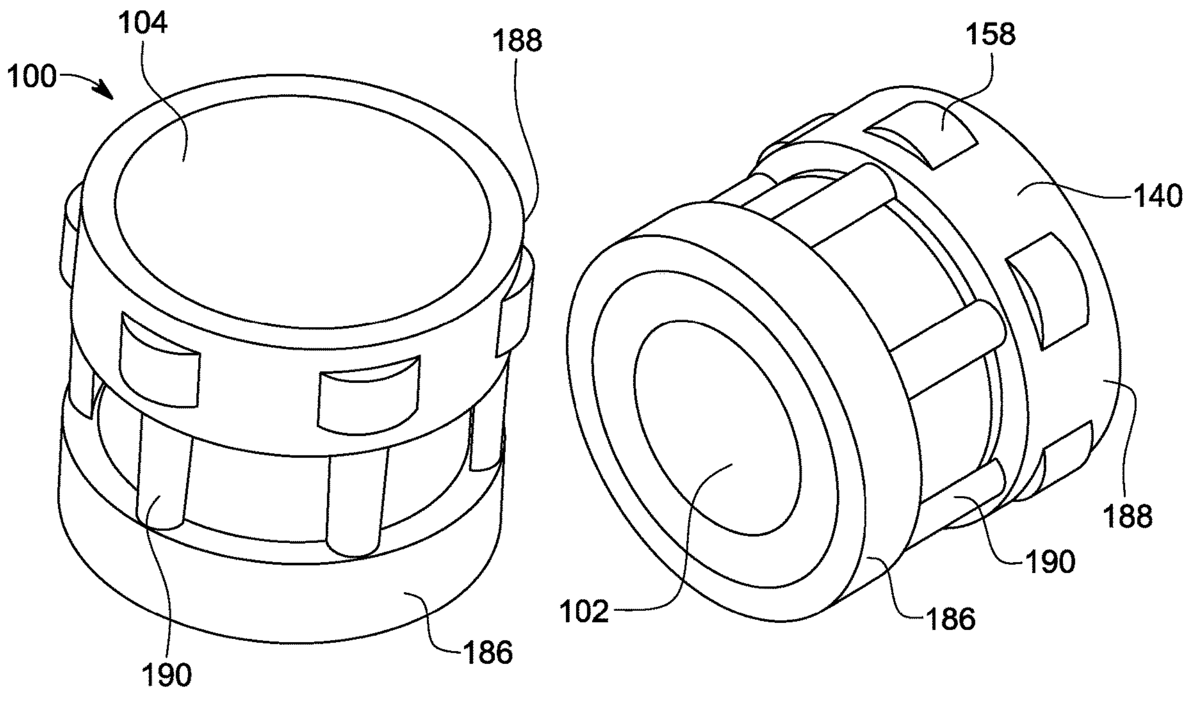
FIG. 23 is a perspective view of a disinfecting cap exemplary embodiment showing a closed end of the cap.
FIG. 24 is a perspective view of the disinfecting cap of FIG. 23 showing an open end of the cap.
Figures 32, 33, 34, 35:
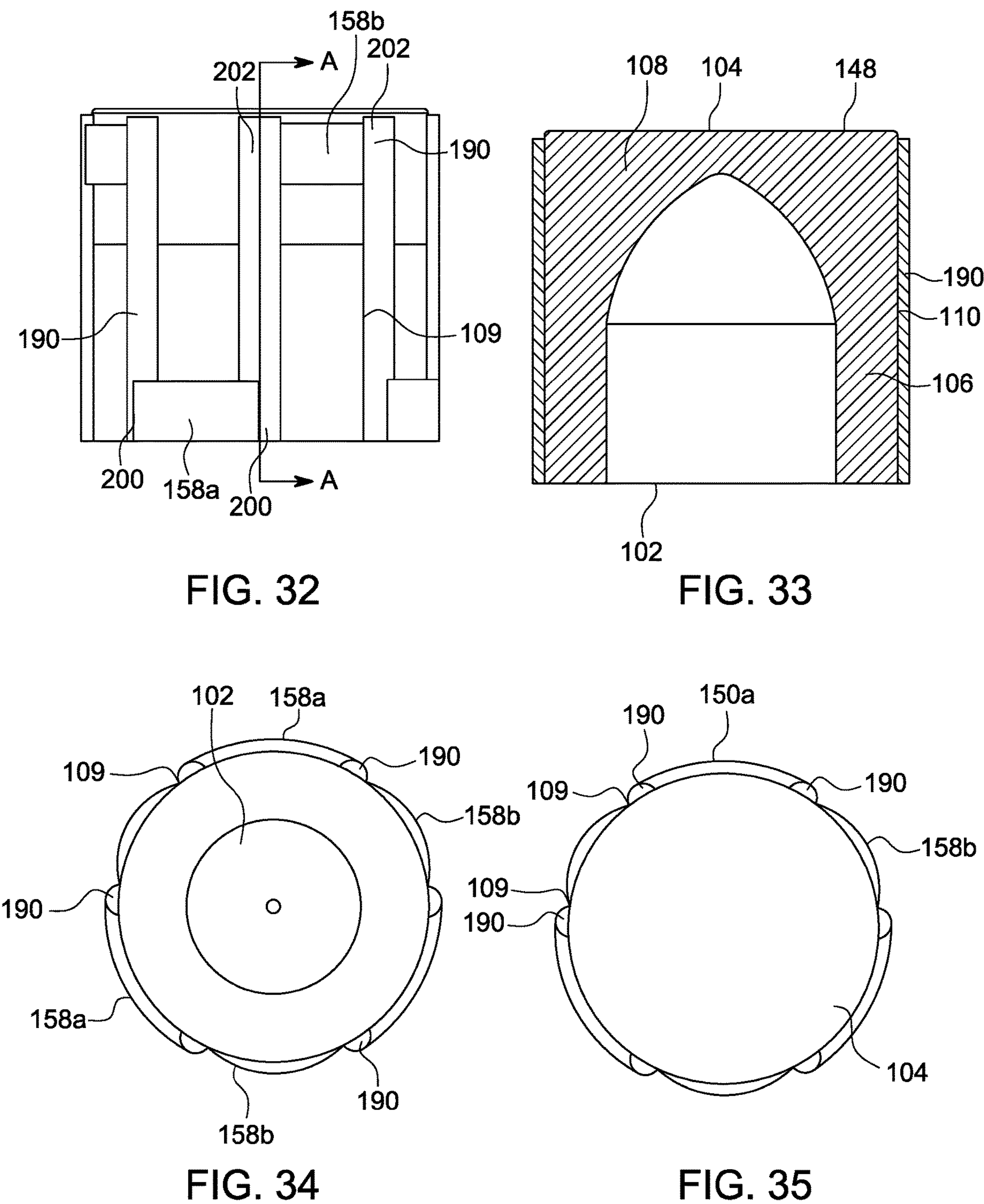
FIG. 32 is a side view of the disinfecting cap of FIG. 30.
FIG. 33 is a cross-sectional view of the disinfecting cap of FIG. 32 along line A-A.
FIG. 34 is an end view of the disinfecting cap of FIG. 30 showing an open end.
FIG. 35 is an end view of the disinfecting cap of FIG. 30 showing a closed end.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, forward and rearward, inside and outside, interior and exterior, and the like may be used solely to distinguish one entity or action from another entity or action without necessarily requiring or implying any actual such relationship, direction or order between such entities or actions.

The terms "proximal" and "distal" may be used in this application when describing various embodiments. These terms are not intended to be limiting and are merely provided for ease of maintaining a consistent orientation when describing various embodiments. As used herein, proximal refers to the direction generally closer to the patient and/or medical device to be cleaned and distal refers to the direction generally farther from the patient and/or medical device to be cleaned.

This application provides a description of various implementations and embodiments of a device for cleaning medical implements, in particular a device for cleaning vascular or other fluid access sites. Various embodiments of the invention include a cap having an opening to receive an access site. Throughout this application illustrative embodiments refer to use of a cap to engage with a "port" as an example of such an access site. One of skill in the art would understand that the invention may also be used in conjunction with other access sites or other medical devices without access sites.

In addition, the terms "open end" and "closed end" may be used in this application when describing various embodiments. These terms are not intended to be limiting and are merely provided for ease of maintaining a consistent orientation when describing various embodiments. As used herein, absent a specific contradictory disclosure, "open end" refers to an end of a cap having an opening into an interior volume into which a port is inserted, regardless of the geometry of the cap. Closed end refers to an end of a cap opposite or separated from the open end and not having an opening for accepting a port.

The following is a non-limiting example of how such a cap may be used by a healthcare worker: the healthcare worker may, with gloved hands, open the cap packaging and place the cap over the port of a medical implement to be cleaned. In certain embodiments, the healthcare worker may wipe the site by either applying a turning motion or by simply pushing the cap onto the port. The cap could then remain secured in place by threads other mechanisms described herein. A cap in place on a medical implement may be a positive indication that a desired site of the medical implement is clean. A vibrant color or other indicia may be used to allow instant visualization of a cap's presence from a door or hallway.

Embodiments of the cap described herein may include a disinfecting substance, such as a solution of a suitable microbiocide or germicide. The disinfecting substance can include an anti-bacterial disinfectant of any suitable type and suitable amount depending upon the size and structure of the cap. For example, in some embodiments the disinfecting substance may be an aqueous solution including about two percent (2%) chlorhexidine gluconate (chlorhexidine solution, "CHG"). In other embodiments, a solution including about 70 percent (70%) isopropyl alcohol ("IPA") in an aqueous solution is included in the disinfecting substance. In yet another embodiment, a solution including about 70 percent (70%) IPA and about two percent (2%) CHG in an aqueous solution is included in the disinfecting substance. In the latter solution, it is recognized that the concentration of IPA can vary from about 60 percent (60%) to about 90 percent (90%) and the concentration of CHG can vary from about one percent (1%) to about five percent (5%), in one embodiment.

Other suitable solution compositions and concentrations are also possible. For instance, povidone iodine, polyhexanide (polyhexamethylene biguanide, "PHMB"), benzalkonium chloride ("BAC"), chlorxylenol ("PCMX") or hydrogen peroxide solutions can be included in the disinfecting substance of further embodiments. Throughout this disclosure, reference to one or more of these disinfecting substances in relation to a cap embodiment should be understood to disclose the use of any other appropriate disinfecting substance as disclosed herein or as would be understood by one of ordinary skill in the art. In addition, embodiments of the disinfecting substance may be in a liquid or a gel form.

In various embodiments of the invention described herein, the port comes in contact with the disinfecting substance in liquid or gel form, or with an absorbent material infused with the disinfecting substance. However, it may not be necessary for the surface of the port to contact the liquid or gel disinfecting substance. For example, if IPA is used as part of a disinfecting solution, IPA vapors trapped within the cap may act as a disinfectant for the port without requiring contact between the liquid solution and the site being cleaned.

Various materials may be used to manufacture the cap embodiments described herein. Appropriate materials may include polyurethane ("PU"), polypropylene ("PP"), polyethylene ("PE"), thermoplastic elastomer ("TPE"), thermoplastic vulcanizate ("TPV") such as Santoprene, or other materials as would be understood by one of ordinary skill in the art. Various embodiments described herein recite the use of particular materials, but one of ordinary skill would understand that other appropriate materials could be substituted for the disclosed material.

Various embodiments also describe the use of sponge or foam material. Such foam may be formed of polyurethane ("PU") or another appropriate absorbent material. Alternatively, other absorbent materials may be used in place of foam, including for example, felted non-woven or other fibrous materials.

FIGS. 1-3 show an illustrative embodiment of a disinfecting cap. The cap 100 may comprise an open end 102 and a closed end 104. A sidewall 106 may extend between the open end and closed end. An end wall 108 may be positioned at the closed end 104 of the cap. An outside surface 110 of the sidewall 106 may be generally cylindrical and may comprise a step 112 such that a first portion 114 of the sidewall has a diameter that is greater a second portion 116 of the sidewall. Alternatively, the first and second portions may have substantially the same diameter, or the first portion of the sidewall may have a diameter that is less than the diameter of the second portion.

The sidewall 106 may encompass an interior volume 118. An interior surface 120 of the sidewall 106 may be generally cylindrical in a first section 122 of the interior volume. Alternatively, the interior volume may have a generally conical cross-section in the first section 122. The interior volume may also comprise a second section 124. The second section may comprise an open end 126 and a closed end 128. A cross-section of the second section 124 may be spherical, semi-spherical, conical, a rounded cone, or some combination of these or other shapes. A distance 107 between the closed end 128 of the second section and the end wall 108 may vary depending on the dimensions of the cap and shape of the second section. A post 130 may extend into the interior space 118 from the closed end 128 of the second section 124.

The disinfection cap 100 may comprise a single material that forms the sidewall 106 and end wall 104 in a single piece. For example, the disinfecting cap 100 may comprise a unitarily molded piece. The cap may be formed of TPV or any other appropriate material.

Figures 71, 72, 73, 74:
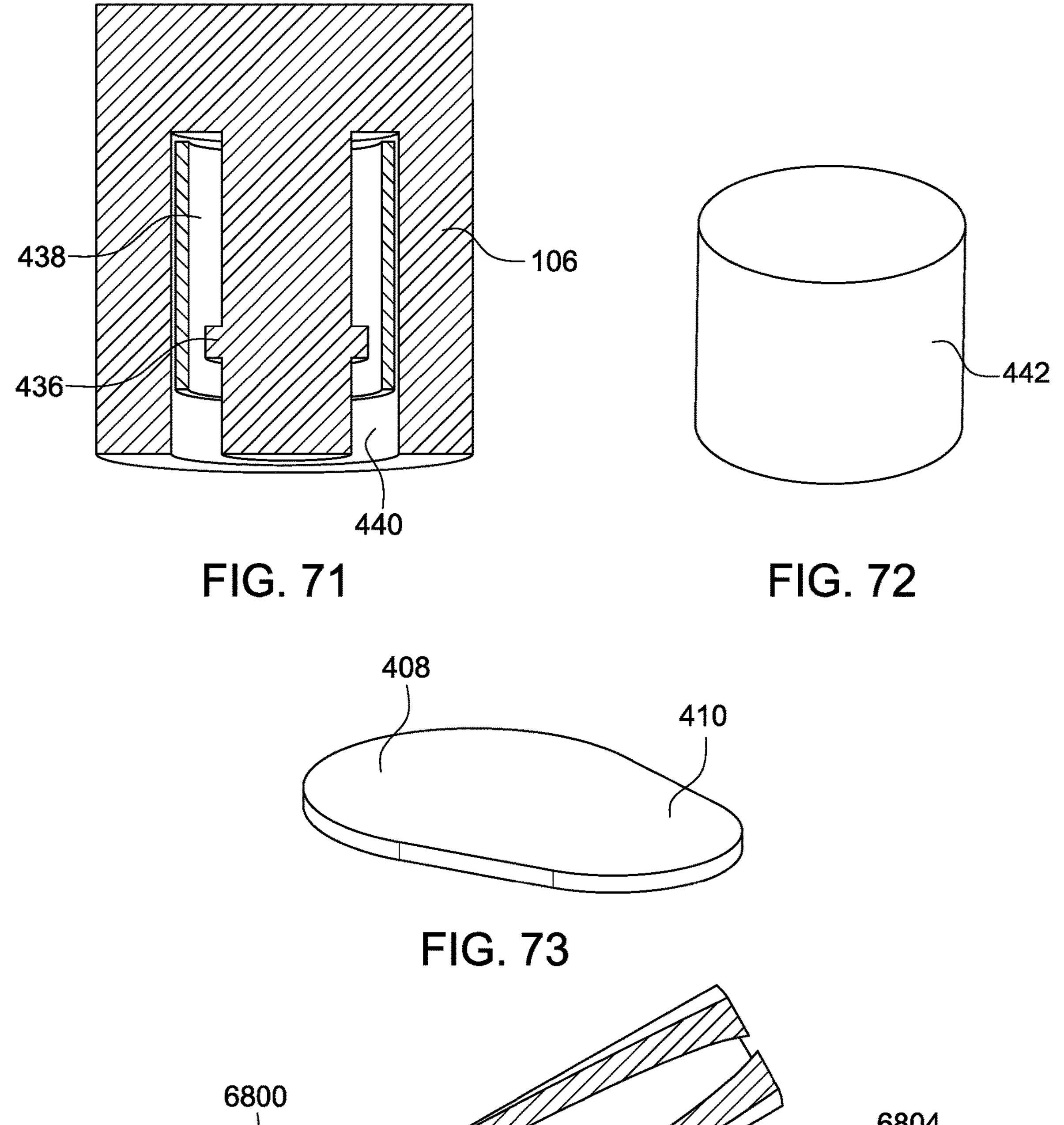
FIG. 71 is a perspective, cross-sectional view of the disinfecting cap of FIG. 69 showing a sponge positioned in the cap.
FIG. 72 is a perspective view of a sponge for use with various embodiments of a disinfecting cap.
FIG. 73 is a perspective view of a foil seal for use with various embodiments of a disinfecting cap.
FIG. 74 is a cross sectional view of a Y-site having a female port.

The cap may further comprise a cover or seal as illustrated in FIG. 73 that extends across the open end 102 of the cap to seal a disinfecting substance and/or an absorbent material within the interior volume. The seal may be positioned adjacent to an end surface 154 of the interior volume 118 or may be spaced some distance into the interior volume, leaving a space between the seal and the end surface. The seal may have a first portion 408 generally shaped and sized to cover the open end 102 of the cap. The seal may further include a grip or tab 410 that aids in removal of the seal from the cap. Alternatively, the seal may include perforations, score lines or other features to aid in fracturing the seal. Such a seal may be any appropriate material including foil, polymer, etc.

The interior surface 120 of the first section 122 may engage an outside surface of a female luer 6802, as shown, for example, in the Y-site 6800 illustrated in FIG. 74. The interior surface 120 of the cap may engage the threads 6804 of the female luer. The engagement may be made by a press or friction fit between an outside edge 6806 of the threads against the cap interior surface 120. In such a press fit, the interior surface of the cap may deform outwardly to accommodate the threads of the female luer. Such deformation may occur by a displacement of some or all the cap sidewall 106 in an outward direction. Alternatively, deformation of the interior surface 120 may occur by compression of the sidewall material without movement or deformation of the outside surface 110. In further alternatives, both compression and movement of the sidewall may occur on inserting the female luer into the cap. Embodiments of the disinfecting cap may incorporate elements similar to those discussed elsewhere in the application but not specifically labeled in or discussed with respect to FIGS. 1-3.

FIGS. 4-6 show a further illustrative embodiment of a disinfecting cap. The cap 100 may comprise an open end 102 and a closed end 104. A sidewall 106 may extend between the open end and closed end. An end wall 108 may be positioned at the closed end 104 of the cap. An outside surface 110 of the sidewall 106 may be generally cylindrical.

The sidewall 106 may encompass an interior volume 118. An interior surface 120 of the sidewall 106 may be generally cylindrical in a first section 122 of the interior volume. Alternatively, the interior volume may have a generally conical cross-section in the first section 122. The interior volume may also comprise a second section 124. The second section may comprise an open end 126 and a closed end 128. A cross-section of the second section 124 may be spherical, conical, a rounded cone, or some combination of these or other shapes. A post 130 may extend into the interior space 118 from the closed end 128 of the second section 124.

The disinfection cap 100 may comprise a skirt 132 that surrounds a least a portion of the sidewall 106. An inside surface 134 of the skirt 132 may be positioned adjacent to the outside surface 110 of the sidewall 106. The inside surface of the skirt may be adhered to the outside surface of the sidewall. A portion 136 of the sidewall 106 may extend around an end 138 of the skirt 132. The flange 142 of the sidewall may extend to cover an outside surface 140 of the skirt. An extension 144 of the flange 142 may engage with a notch or channel 146 formed in an outer surface 140 of the skirt. The notch 146 may extend around a portion or substantially the entire circumference of the skirt. The flange 142 and notch 146 may be formed adjacent or near the closed end 104 of the cap. Alternatively, one or more tabs may extend from the skirt 132 or sidewall flange 142 that engage with corresponding indentations or the like that are formed in the corresponding surface of the sidewall extension or skirt. The skirt 132 may extend along the sidewall 106 of the cap to the open end 102. An open-end surface 152 of the skirt may be coplanar with an end surface 154 of a cap body 148 at an open end 102 of the cap. In this manner, the skirt end surface 152 and cap body end surface 154 may form concentric rings at an open end of the cap.

The cap body 148 of the cap may be formed of a first material. This material may be TPV, PU, or another appropriate material. The skirt 132 may be formed of a second material. In embodiments of the cap, the second material has a higher durometer than the first material. The second material may be PP, PE, or another appropriate material.

The interior surface 120 of the first section 122 may engage an outside surface of a female luer 6802, as shown, for example, in the Y-site 6800 illustrated in FIG. 74. The interior surface 120 of the cap may engage the threads 6804 of the female luer. The engagement may be made by a press or friction fit between an outside edge 6806 of the threads against the cap interior surface 120. In such a press fit, the interior surface of the cap may deform outwardly to accommodate the threads of the female luer. Such deformation may occur by a displacement of some or all the cap sidewall 106 in an outward direction. Alternatively, deformation of the interior surface 120 may occur by compression of the sidewall material without movement or deformation of the outside surface 110. In further alternatives, both compression and movement of the sidewall may occur on inserting the female luer into the cap.

The skirt 132 may constrain or provide reinforcement to the cap body 148. In embodiments of the cap, the skirt may reduce or eliminate any expansion of the cap when a female luer is inserted; the skirt may increase the pressure exerted by the cap against the luer, which may result in an increased force necessary to remove the cap once it is positioned on the luer; or the skirt may have both these effects. An outer surface 140 of the skirt may comprise protuberances that extend from the outer surface such as columns 156 or tabs 158 as described in more detail elsewhere in the application. Embodiments of the disinfecting cap may incorporate elements similar to those discussed elsewhere in the application but not specifically labeled in or discussed with respect to FIGS. 4-6.

FIGS. 7-11 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The disinfection cap 100 may comprise a skirt 132 that surrounds a least a portion of the sidewall 106. A skirt flange 160 may interlock or otherwise engage with a groove 162 of the cap body 148. The skirt flange 160 may have a cross section that is narrower than the cross section of skirt wall 300 of the skirt body 302. The flange may comprise a stepped engagement ring 304 or discrete tabs that extend outward from the flange sidewall. The engagement ring 304 may engage a corresponding cavity 306 formed in the cap body groove 162 and may comprise a tab or extension 305. Alternatively, the cap may comprise other engagement elements formed on the skirt flange 160 that engage with corresponding elements formed in the body groove 162, including tabs, serrations, threads, or the like.

In embodiments of the cap, the cap body may have a first section 312 having a first diameter, and second section 314 having a second diameter that engages an inner diameter/surface 316 of the skirt. The inner surface of the skirt may be generally cylindrical or may be in the shape of a truncated cone with the open end 384 of the surface 316 having a smaller diameter than the closed end 386. A flange 142 of the cap body 148 may extend beyond an outer surface 310 of the skirt body 302. Tabs 158 may extend from the skirt outer surface 310 beyond the outer surface 308 of the cap body 148. Embodiments of the disinfecting cap may incorporate elements similar to those discussed above but not specifically labeled in or discussed with respect to FIGS. 7-11.

FIGS. 12-16 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The disinfection cap 100 may comprise a skirt 132 that surrounds a least a portion of the sidewall 106. An outer surface 308 of the of the cap body sidewall may have a uniform, cylindrical outside diameter 318 that engages an inner diameter 316 of the skirt. A section 164 of the cap body sidewall 106 may extend beyond a bottom edge 166 of the skirt. Embodiments of the disinfecting cap may incorporate elements similar to those discussed elsewhere in the application but not specifically labeled in or discussed with respect to FIGS. 12-16.

FIGS. 17-22 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The disinfection cap 100 may comprise a framework 168 that is positioned within or embedded in the sidewall 106 such that a part 176 of the sidewall is inside the framework and a part 178 of the sidewall is outside the framework. Alternatively, the framework may be positioned around an outer surface 170 of the sidewall 106, and a secondary sidewall 172 may surround a framework outer surface 174. The framework may include voids or through holes (not shown) that are filled by the material of the cap body 148 allowing the framework 168 to interlock with the cap body. An open-end surface 180 of the framework 168 may be coplanar with an end surface 154 of a cap body 148 at an open end 102 of the cap. In this manner, the framework end surface 180, the cap body inside part end surface 182, and the cap body outside part end surface 184 may form concentric rings at an open end of the cap. A section 192 of the framework may be concentric with or otherwise exposed at an outside surface 110 of the sidewall 106. Columns 156 and/or tabs 158 may extend from the exposed section 192. Embodiments of the disinfecting cap may incorporate elements similar to those discussed elsewhere in the application but not specifically labeled in or discussed with respect to FIGS. 17-22.

FIGS. 23-28 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The disinfection cap 100 may comprise a first ring 186 that surrounds a least a portion of the sidewall 106. The first ring may be positioned near or adjacent the open end 102 of the cap. The cap may further comprise a second ring 188 that surrounds a least a portion of the sidewall 106. The second ring may be positioned adjacent the closed end 102 of the cap or nearer to the closed end relative to the first ring. Columns 190 may extend between the first ring 186 and the second ring 188. Tabs 158 may extend from an outer surface 140 of one or both rings. The columns may comprise an outer surface 322 having a generally semi-circular cross-section and an inner surface 320 that conforms to the outer surface 308 of the cap body. The column outer surface 322 may be recessed such that an outer surface 324 of the first ring 186 and an outer surface 326 of the second ring 188 extend beyond the surface 322 of the columns. The columns 190 may have a tapered cross section such that the column has a greater cross-sectional area at a first end 328 than at a second end 330. The first and second rings may have the same outside diameter. Alternatively, the first and second rings may have different outside diameters. Embodiments of the disinfecting cap may incorporate elements similar to those discussed elsewhere in the application but not specifically labeled in or discussed with respect to FIGS. 23-28.

FIG. 29 show a further illustrative embodiment of the disinfecting cap of FIGS. 23-28. In this embodiment, one or more of the rings 186, 188 may comprise an inwardly extending flange 194. The flange may engage a groove 196 formed in an outside surface 110 of the cap body 148.

FIGS. 30-35 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The disinfection cap 100 may comprise columns 190 extending along and from an outer surface 110 of the cap body. Tabs 158 may extend along or from the outer surface 110 of the cap body 148 in a space 198 between the columns 190. The tabs 158 may attach adjacent first ends 200 or adjacent second ends 202 of the columns 190. Tabs may alternate between attaching first ends 200 and second ends 202. Tabs 158*a* may extend from a centerline of adjacent columns 190. Alternatively, tabs 158*b* may extend from an edge 159 or near to an edge of adjacent columns 190. Both tab configurations 158*a*, 158*b* may be used. For example, longer tabs 158*a* may be used adjacent to the open end 102 of the cap body 148, and shorter tabs 158*b* may be used adjacent to the closed end 104 of the cap body. Embodiments of the disinfecting cap may incorporate elements similar to those discussed elsewhere in the application but not specifically labeled in or discussed with respect to FIGS. 30-35.

As particularly illustrated in FIGS. 36 and 37 and as shown in other figures, an outer surface 140 of the skirt may comprise protuberances that extend from the outer surface such as columns 156 or tabs 158. The columns 156 may be of various lengths, heights, and thicknesses and may vary in number and positioning. The columns 156 may extend a full length of the exposed outside surface 334 of the skirt from a lower edge 332 of the exposed section to an upper edge 336. Alternatively (see, e.g., FIGS. 4-6), the columns may extend from a lower edge 332 of the exposed section 334 of the skirt for a distance that does not extend to the upper edge 336. The columns may provide for an enhanced grip by the user to improve control and manipulation of the cap. The tabs 158 may be of various lengths and heights and may vary in number and positioning. For example, the tabs may be positioned adjacent to the lower edge 332 of the skirt exposed section 334. Alternatively, the tabs may be spaced apart some distance 338 from the lower edge 332. A tab 158 may extend from one column 156*a* to an adjacent column 156*b*. Alternatively, the tab may extend a distance less than the space between columns (see, e.g., FIGS. 4-6). The tabs may allow the cap to engage with other devices. For example, if the cap is positioned in a cavity of a syringe plunger, the tabs 158 may interlock with features of the plunger cavity to secure the cap in position until the cap is to be used on a site.

FIGS. 38-43 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The disinfection cap 100 may comprise a skirt 132 that surrounds a least a portion of the sidewall 106. The skirt 132 may comprise a skirt side wall 340 and a skirt end wall 346. The skirt may further comprise an outer surface 140. The outer surface 140 of the skirt may comprise protuberances that extend from the outer surface such as columns 156 or tabs 158 as described in more detail elsewhere in the application. The skirt may further comprise an open end 342 and a closed end 344. The closed end may have an end wall 346. Holes, channels, or apertures 348 may extend through the end wall 346. The end wall 346 may be generally planar, while an upper or inside surface 352 of the end wall may have a convex shape. The convex shape may be at least partially spherical or may be formed in a truncated cone shape. The inside surface 352 may have a generally planar portion 354 at a center of the inside surface. The skirt outer surface 140 may comprise a lower surface 350 of the end wall and may further comprise a step 356 between a first, upper section 358 having a first diameter and a base section 360 having different diameter. The diameter of the base section may be smaller than the diameter of the upper section.

The cap body 148 may comprise a cavity portion 362 and a flange portion 364. The cavity portion may comprise a cavity or interior volume 118 extending from the open end 102. The cavity portion may have a sidewall 106 that is surrounded, at least in part, by wall 300 of the skirt 132 such that an outside surface 366 of the cavity portion sidewall 106 is adjacent to an inner diameter 316 of the skirt sidewall 340. Pillars or extensions 368 may extend from an outer bottom surface 370 or the cavity portion 362. The pillars 368 extend through channels 348 formed in the skirt end wall 346.

The pillars 368 may connect the cavity portion 362 with the flange portion 364. The flange portion may comprise a bottom or end wall 380 having an inner surface 372, an outer surface 374, and a sidewall 376 extending from an edge 378 of the bottom wall in a direction toward the open end of the cavity portion. The sidewall 376 may be spaced and sized such that it surrounds the base section 360 of the skirt 132. An end surface 382 of the sidewall 376 may contact or be positioned proximate the skirt step 356. The pillars 368 may extent from the base section 360 inner surface 372 through the channels in the skirt end wall 346. Embodiments of the disinfecting cap may incorporate elements similar to those discussed above but not specifically labeled in or discussed with respect to FIGS. 38-43.

The cap body cavity portion 362 and flange portion may be integrally formed. In an illustrative method of manufacturing, the skirt 132 may be injection molded from an appropriate material as discussed elsewhere in the application. The cap body 148 may then be overmolded by injection molding onto the skirt in a secondary operation. The channels 348 through the skirt allow the cap body portions to be molded in a single piece and provide for an interlocking engagement between the cap body and the skirt.

FIGS. 44-71 illustrate additional embodiments or features of a disinfecting cap. These features and embodiments may incorporate elements or features of other cap embodiments discussed herein or may be incorporated into such other embodiments.

As illustrated in FIGS. 44-45, an open end surface 152 of the skirt may be coplanar with an end surface 154 of a cap body 148 at an open end 102 of the cap 100. The cap body may provide for a transition from the interior surface 120 of the interior volume 118 to the end surface 154 of the cap body. The transition may comprise a chamfer 388 (FIG. 44). The chamfer 388 may extend from the interior surface 120 to the outside surface 110 of the sidewall 106 such that the chamfer forms the entire end surface 154 of the cap body. Alternatively, the chamfer may extend across only a portion of the end surface such that a section of the end surface is coplanar with the end surface 152 of the skirt. The transition may comprise a fillet 390 (FIG. 45). The fillet may be sized such that a section 392 of the end surface is coplanar with the end surface 152 of the skirt. Alternatively, the fillet may be sized such that the fillet extends across substantially the entire end surface 154 of the cap body.

FIGS. 46-47 show a further illustrative embodiment of a disinfecting cap. The cap 100 may comprise a cap body 148 having an open end 102 and a closed end 104. A sidewall 106 may extend between the open end and closed end. An end wall 108 may be positioned at the closed end 104 of the cap. The cap may comprise a membrane 204 that extends at least partial across the opening formed at the open end 102 of the cap. The membrane may comprise a hole 206 formed at its center. The membrane may comprise an elastomeric material that allows displacement of the membrane so that a site can be inserted into the cap. The membrane may be spaced some distance 402 below an end surface 154 of the cap.

The cap may further comprise a sponge 394 or other absorbent material that is placed in the interior 118 of the cap. The sponge may comprise a central cavity 396. The sponge may be cylindrical with an outside diameter such that an outside surface 398 of the sponge is proximate an interior surface 120 of the cap. The central cavity may extend from a top surface 400 of the sponge for a distance that is less than the full thickness of the sponge. Alternatively, the central cavity may extend through the entire thickness of the sponge.

FIGS. 48-49 show further embodiments of a disinfecting cap. The cap 100 may comprise a membrane 204 that extends at least partial across the opening formed at the open end 102 of the cap. The membrane may comprise a slit 210 formed at or extending over a center point 212 of the membrane. The membrane may be positioned such that the membrane is coplanar with the end surface 154 of the cap.

FIGS. 50-51 show further embodiments of a disinfecting cap. The cap 100 may comprise a membrane 204 that extends at least partial across the opening formed at the open end 102 of the cap. The membrane may comprise multiple slits 210*a*, 210*b*. One or more of the slits may extend over a center point 212 of the membrane. The slits may intersect at the center point. The slits may extend at a 90° angle relative to one another within the plane of the membrane. The membrane may comprise an elastomeric material that allows displacement of the membrane so that a site can be inserted into the cap.

FIG. 52 show a further illustrative embodiment of a disinfecting cap. The cap 100 may comprise a cap body 148. The cap body may include a first section 214 and a second section 216. A hinge 218 connects the first and second body sections 214, 216 such that the cap may be snapped around a site. Each body section may contain a portion of a membrane 220. The membrane portions may include cutouts 222. The membrane may separate a first cavity 404 of the cap 100 from a second cavity 406. One or more sponges 394 may be positioned in the second cavity. The cap may comprise a latch or other engaging elements that secure the cap in a closed position.

FIGS. 53-55 show a further illustrative embodiment of a disinfecting cap. The cap 100 may comprise an open end 102 and a closed end 104. A sidewall 106 may extend between the open end and closed end. An end wall 108 may be positioned at the closed end 104 of the cap. An outside surface 110 of the sidewall 106 may be generally cylindrical.

The disinfection cap 100 may comprise a shell 224 that surrounds a least a portion of the sidewall 106 and the end wall 108. An inside surface 226 of the shell 224 may be positioned adjacent to the outside surface 110 of the sidewall 106. The inside surface of the shell may be adhered to the outside surface of the sidewall. A flange 228 may extend from an outside surface of the cap body end wall 108. The flange 228 may engage a groove 230 formed at an inside surface 232 of the shell 224. The flange 228 may be spaced from the cap body end wall 108 by a post section 236 that corresponds to a hole 238 formed in the shell inside surface 232.

An open-end surface 234 of the shell may be coplanar with an end surface 154 of a cap body 148 at an open end 102 of the cap. In this manner, the shell end surface 234 and cap body end surface 154 may form concentric rings at an open end of the cap.

FIGS. 56-58 show a further illustrative embodiment of a disinfecting cap. The cap 100 may comprise an open end 102 and a closed end 104. A sidewall 106 may extend between the open end and closed end. An end wall 108 may be positioned at the closed end 104 of the cap. An outside surface 110 of the sidewall 106 may be generally cylindrical.

The disinfection cap 100 may comprise a shell 224 that surrounds a least a portion of the sidewall 106 and the end wall 108. An inside surface 226 of the shell 224 may be positioned adjacent to the outside surface 110 of the sidewall 106. The inside surface of the shell may be adhered to the outside surface of the sidewall.

FIGS. 59-71 illustrate additional configuration of embodiments of the cap as discussed throughout the application. These configurations disclose different features of the embodiments, and caps consistent with these configurations may have a unitary construction as discussed with regard to the embodiment of FIGS. 1-3 or may have a two-part construction as discussed with regard to the embodiment of FIGS. 4-6 and others.

Figures 59, 60, 61, 62:
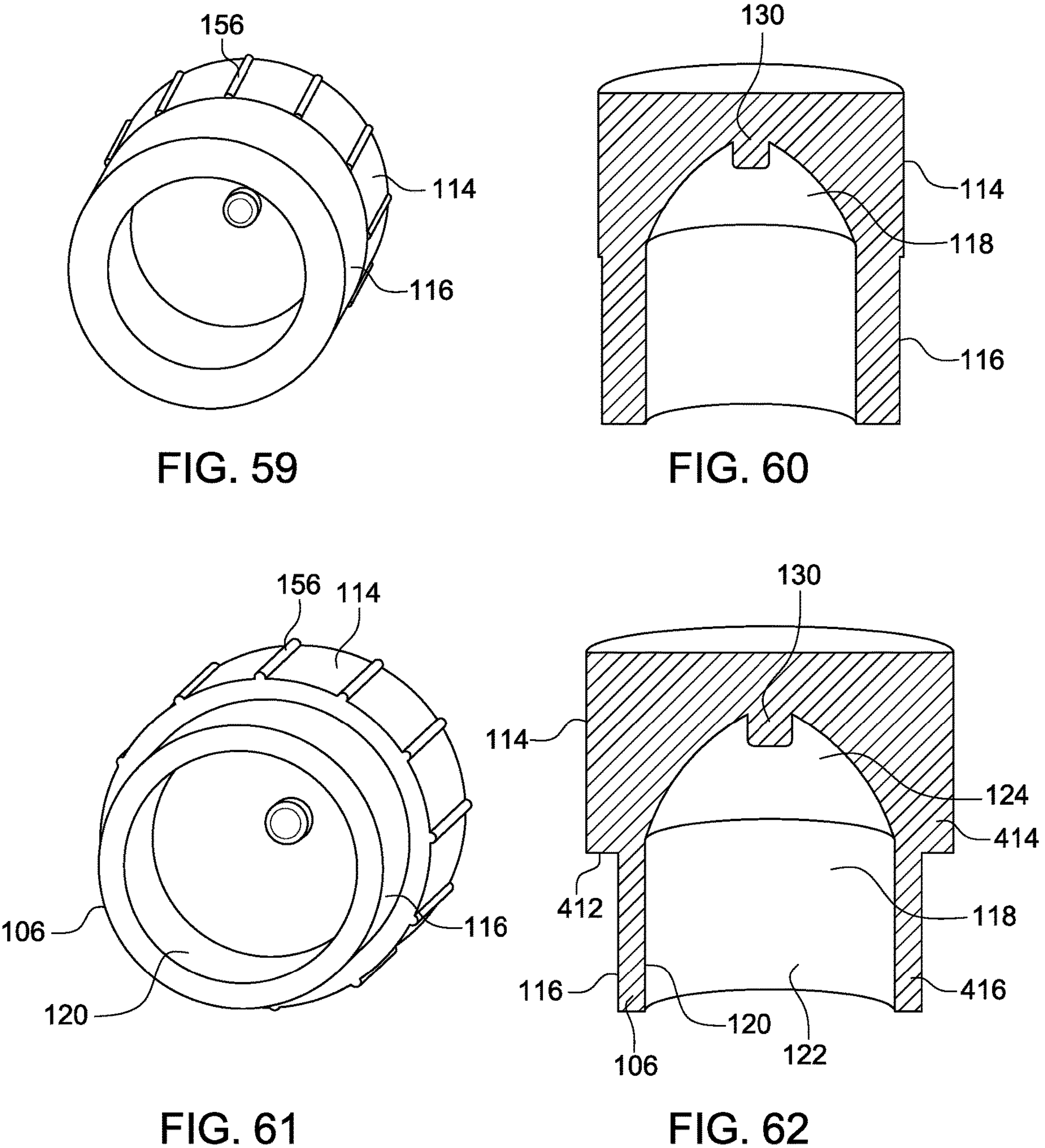
FIG. 59 is a perspective view of a disinfecting cap exemplary embodiment showing an open end of the cap.
FIG. 60 is a perspective, cross-sectional view of the disinfecting cap of FIG. 59.
FIG. 61 is a perspective view of a disinfecting cap exemplary embodiment showing an open end of the cap.
FIG. 62 is a perspective, cross-sectional view of the disinfecting cap of FIG. 61.

FIGS. 59-60 illustrate an embodiment in which columns 156 extend from a first portion 114 of the sidewall but do not extend to a second portion 116. A post 130 may extend into the interior space 118. Apart from the columns 156, the first 114 and second 116 portions have substantially the same cross section. Other features of the embodiment will be apparent from the figures.

FIGS. 61-62 illustrate an embodiment in which columns 156 extend from a first portion 114 of the sidewall but do not extend to a second portion 116. A post 130 may extend into the interior space 118. The first 114 portion has a diameter that is larger than the second section such that a step 412 is formed between the sections. The sidewall 414 of the first portion is thicker than the sidewall 416 of the second portion 116. An interior surface 120 of the sidewall 106 may be generally cylindrical in a first section 122 of the interior volume. The interior volume may also comprise a second section 124. A cross-section of the second section 124 may have a rounded conical shape. Other features of the embodiment will be apparent from the figures.

Figures 63, 64, 65, 66:
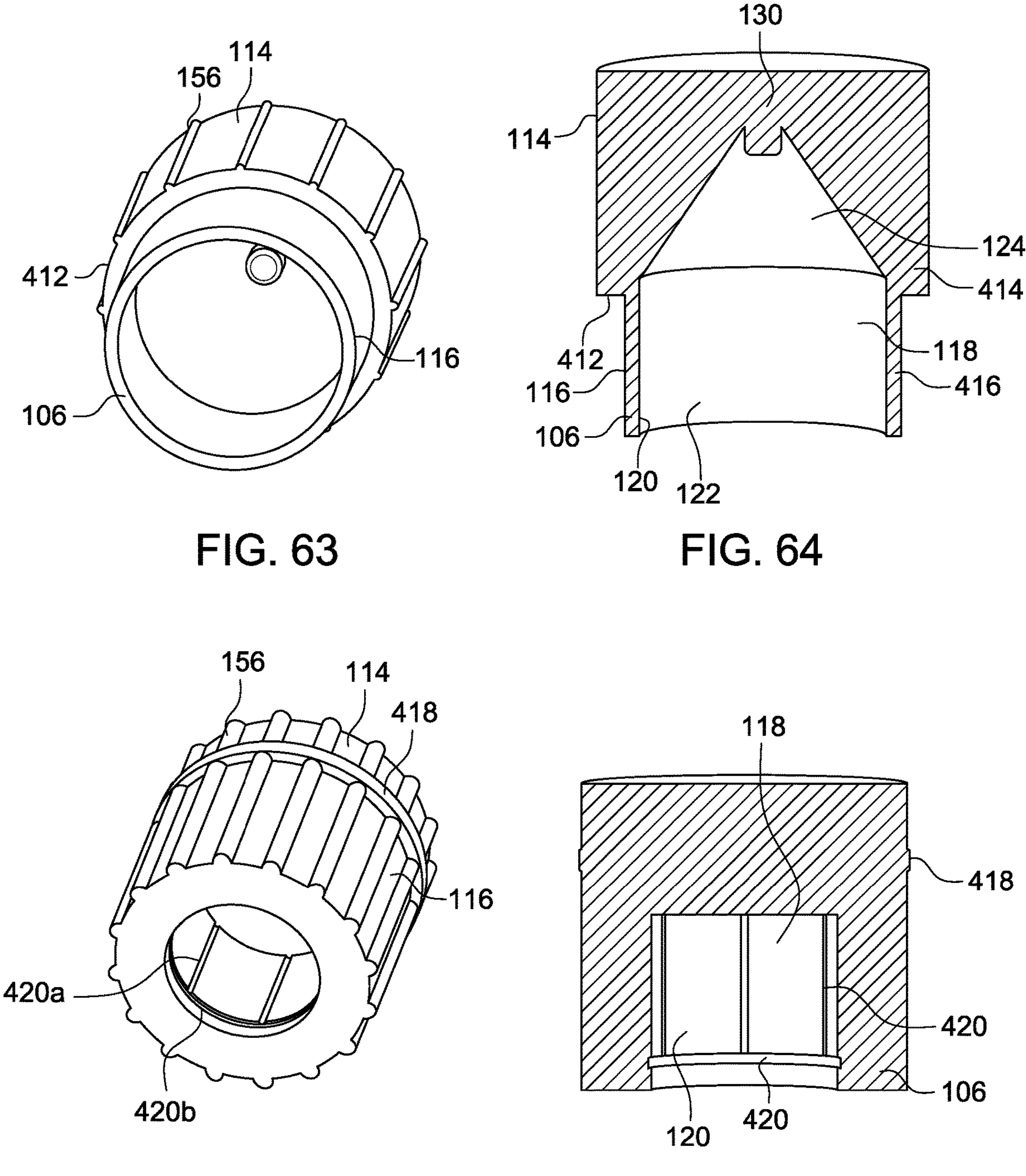
FIG. 63 is a perspective view of a disinfecting cap exemplary embodiment showing an open end of the cap.
FIG. 64 is a perspective, cross-sectional view of the disinfecting cap of FIG. 63.
FIG. 65 is a perspective view of a disinfecting cap exemplary embodiment showing an open end of the cap.
FIG. 66 is a perspective, cross-sectional view of the disinfecting cap of FIG. 65.

FIGS. 63-64 illustrate an embodiment in which columns 156 extend from a first portion 114 of the sidewall but do not extend to a second portion 116. A post 130 may extend into the interior space 118. The first 114 portion has a diameter that is larger than the second section such that a step 412 is formed between the sections. The sidewall 414 of the first portion is thicker than the sidewall 416 of the second portion 116. An interior surface 120 of the sidewall 106 may be generally cylindrical in a first section 122 of the interior volume. The interior volume may also comprise a second section 124. A cross-section of the second section 124 may have a conical shape. Other features of the embodiment will be apparent from the figures.

FIGS. 65-66 illustrate an embodiment in which columns 156 extend from a first portion 114 of the sidewall and a second portion 116. A raised ring or divider 418 may extend from the outer surface of the cap between the first 114 and second 116 portions. The divider 418 may have a diameter that extends beyond the surface of columns 156. Alternatively, the divider may have a diameter that is coextensive with the highest point of the columns. An interior surface 120 of the sidewall 106 may be generally cylindrical. The interior surface 120 may comprise channels or grooves 420 formed in the surface. A groove 420*b* may extend concentrically around the interior volume 118 and/or a groove 420*a* may extend longitudinally along the interior surface. Other features of the embodiment will be apparent from the figures.

FIGS. 67-68 illustrate an embodiment in which a portion 422 the cap sidewall 106 comprises an interior section 424 and an exterior section 426 that are separated by an annular cavity 428. The interior section 424 of the sidewall may flex outwardly when a site is inserted into the cap in order to accommodate and secure the site. Other features of the embodiment will be apparent from the figures.

FIGS. 69-71 illustrate an embodiment in which a central post 430 extends from the center of a bottom surface 432 at the closed end 128 of the cap 100. The post may extend from the bottom surface to the open end 102 of the cap such that a top surface 434 of the post is coplanar with an end surface 154 of the side wall 106, thereby forming and annular interior space 440. A ring or tab protrusions 436 may extend from a side surface 438 of the post. The protrusions 436 may be positioned between the interior space bottom surface 432 and the post top surface 434. An annular sponge 438 may be positioned in the annular interior space 440. Other features of the embodiment will be apparent from the figures.

FIG. 72 illustrates an embodiment of a foam material or sponge 442 that may be positioned within the interior volume 118 of various embodiments of the cap 100. The sponge may be generally cylindrical as shown or, alternatively, cubical, spherical, or another appropriate shape.

Although a few embodiments have been described in detail above, other modifications are possible. For instance, any of the embodiments described above may be sized and scaled for a particular medical implement, such as a stethoscope or otoscope. Other embodiments may be within the scope of the following claims.

This application provides a description of various implementations and embodiments of a device for cleaning medical implements. The various embodiments have been described as having a variety of features. It will be understood by one of ordinary skill in the art that features of the various embodiments are intended to be interchangeable, and features described in the context of one embodiment may be implemented in conjunction with a device having the features and structure of another embodiment.

What is claimed is:

1. A disinfecting cap for attachment to a port of a medical implement, the cap comprising:

a cap body comprising:

a cavity portion comprising an open end, a closed end, and a sidewall extending between the open end and the closed end, the side wall at least partially enclosing an interior cavity, a flange portion, a first pillar extending between the cavity portion and the flange portion, and a second pillar separate from the first pillar extending between the cavity portion and the flange portion;

a skirt comprising a skirt sidewall, a skirt end wall, an outer surface, a first aperture, and a second aperture;

wherein the skirt covers at least a portion of an exterior surface of the cap body cavity portion;

wherein the cap body flange portion covers at least a portion of the outer surface of the skirt; and wherein the cap body first pillar extends through the skirt first aperture and the cap body second pillar extends through the skirt second aperture.

2. The disinfecting cap of claim 1, wherein the cap body first pillar is a solid pillar.

3. The disinfecting cap of claim 1, wherein the skirt sidewall surrounds at least a portion of the cap body cavity portion sidewall.

4. The disinfecting cap of claim 1, wherein the cap body flange portion comprises a flange portion end wall that covers at least a portion of the skirt end wall.

5. A disinfecting cap for attachment to a port of a medical implement, the cap comprising:

a cap body comprising:

a cavity portion comprising an open end, a closed end, and a sidewall extending between the open end and the closed end, the side wall at least partially enclosing an interior cavity, a flange portion connected with the cavity portion at the cavity portion closed end, the flange portion comprising a flange portion sidewall, and a pillar extending between the cavity portion and the flange portion;

a skirt comprising:

a skirt open end, a skirt end wall comprising an aperture, and a skirt sidewall comprising a first section adjacent the skirt open end and a base section spaced apart from the skirt open end;

wherein the skirt covers at least a portion of an exterior surface of the cap body cavity portion; and wherein the cap body flange portion sidewall surrounds an outer surface of the skirt sidewall base section.

6. The disinfecting cap of claim 5, wherein the cap body comprises a first material having a first durometer, and wherein the skirt comprises a second material having a second durometer different from the first durometer.

7. The disinfecting cap of claim 6, wherein the second durometer is greater than the first durometer.

8. The disinfecting cap of claim 5, wherein the skirt first aperture comprises a channel extending from a skirt end wall inside surface to a skirt end wall outer surface.

9. The disinfecting cap of claim 5, wherein the cap body cavity portion, the flange portion, and the pillar are integrally formed in a single piece of a single material.

10. The disinfecting cap of claim 5, the cap body cavity portion sidewall comprises a smooth, non-threaded interior surface.

11. The disinfecting cap of claim 10, wherein the cap body cavity portion sidewall interior surface engages a thread of a port of the medical implement when the port is inserted into the cap.

12. The disinfecting cap of claim 5, wherein an outside surface of the cap body cavity portion is adjacent to an inner diameter of the skirt sidewall.

13. The disinfecting cap of claim 5, wherein the skirt sidewall first section has a first outside diameter and the skirt sidewall base section has a second outside diameter different from the first outside diameter.

14. The disinfecting cap of claim 13, wherein the first outside diameter is greater than the second outside diameter.

15. The disinfecting cap of claim 14, wherein the skirt sidewall comprises a step between the skirt sidewall first section and the skirt sidewall base section.

16. The disinfecting cap of claim of claim 15, wherein a thickness of the cap body flange portion is less a depth of the step such that an outside diameter of the cap body flange is less than the skirt sidewall first section first outside diameter.

17. The disinfecting cap of claim 5, wherein an inside surface of the skirt end wall comprises a convex shape.

18. The disinfecting cap of claim 17, wherein inside surface of the skirt end wall comprises a planar portion at a center of the inside surface.

19. The disinfecting cap of claim 18, wherein:

the skirt end wall aperture is a first aperture;

the skirt end wall comprises a second aperture;

the cap body pillar is a first pillar extending through the skirt end wall first aperture between the cavity portion and the flange portion;

the cap body further comprises a second pillar separate from the first pillar and extending through the skirt end wall second aperture between the cavity portion and the flange portion;

the first pillar is spaced apart from the skirt end wall inside surface planar portion; and the second pillar is spaced apart from the skirt end wall inside surface planar portion and from the first pillar.

* * * * *